(12) United States Patent
Bohl et al.

(10) Patent No.: US 10,813,631 B1
(45) Date of Patent: Oct. 27, 2020

(54) NON-METALLIC RETRACTOR DEVICE WITH A RATCHET ARM

(71) Applicant: Dignity Health, San Francisco, CA (US)

(72) Inventors: Michael Bohl, San Francisco, CA (US); Zachary Hanze, San Francisco, CA (US); Kevin Baumann, San Francisco, CA (US); Megan Pottinger, San Francisco, CA (US); David Xu, San Francisco, CA (US)

(73) Assignee: Dignity Health, San Francisco, CA (US)

(*) Notice: Subject to any disclaimer, the term of this patent is extended or adjusted under 35 U.S.C. 154(b) by 36 days.

(21) Appl. No.: 16/463,673

(22) PCT Filed: Nov. 22, 2017

(86) PCT No.: PCT/US2017/063099
§ 371 (c)(1),
(2) Date: May 23, 2019

(87) PCT Pub. No.: WO2018/098345
PCT Pub. Date: May 31, 2018

Related U.S. Application Data

(60) Provisional application No. 62/425,712, filed on Nov. 23, 2016, provisional application No. 62/514,074, filed on Jun. 2, 2017.

(51) Int. Cl.
A61B 17/02 (2006.01)
A61B 17/00 (2006.01)
A61M 27/00 (2006.01)

(52) U.S. Cl.
CPC ...... *A61B 17/0218* (2013.01); *A61B 17/0206* (2013.01); *A61B 2017/00407* (2013.01); *A61B 2017/00424* (2013.01); *A61B 2017/00526* (2013.01); *A61M 27/002* (2013.01)

(58) Field of Classification Search
CPC .................. A61B 17/0218; A61B 17/0206
See application file for complete search history.

(56) References Cited

U.S. PATENT DOCUMENTS

| 5,788,630 | A | * | 8/1998 | Furnish | A61B 17/0206 600/232 |
| 5,846,194 | A | | 12/1998 | Wasson | |
| 6,840,492 | B1 | | 1/2005 | Boyne-Aitken | |
| 8,313,430 | B1 | * | 11/2012 | Pimenta | A61B 17/0206 600/202 |
| 2001/0041828 | A1 | * | 11/2001 | Deckman | A61B 17/0206 600/232 |
| 2002/0099268 | A1 | | 7/2002 | Paul | |
| 2004/0204710 | A1 | | 10/2004 | Patel | |
| 2012/0245431 | A1 | * | 9/2012 | Baudouin | A61B 17/0293 600/213 |

(Continued)

OTHER PUBLICATIONS

International Search Report and Written Opinion from corresponding Application No. PCT/US2017/063099, dated Feb. 14, 2018, 14 pages.

*Primary Examiner* — Christian A Sevilla
(74) *Attorney, Agent, or Firm* — Polsinelli PC

(57) ABSTRACT

Various embodiments of a non-metal retractor device having a ratchet arm for retracting an incision and retaining a shunt are described herein.

13 Claims, 19 Drawing Sheets

(56) References Cited

U.S. PATENT DOCUMENTS

2014/0133173 A1\* 5/2014 Vayser ................ F21V 33/0068
    362/572
2015/0094533 A1\* 4/2015 Kleiner .............. A61B 1/00103
    600/109

\* cited by examiner

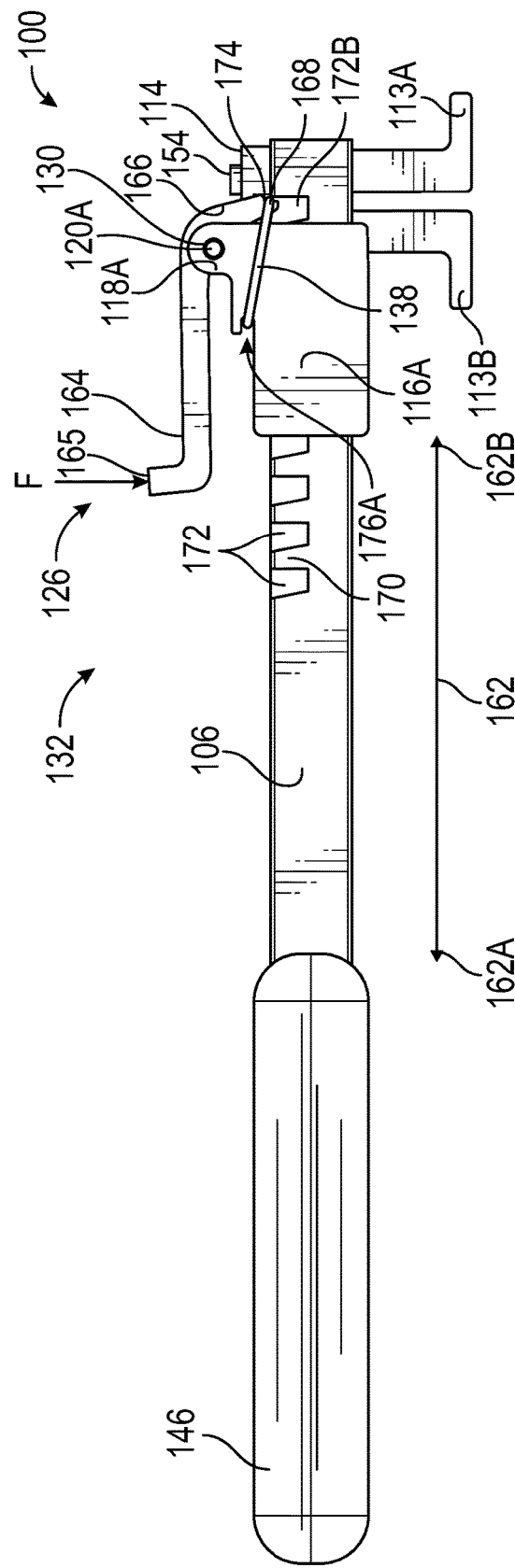
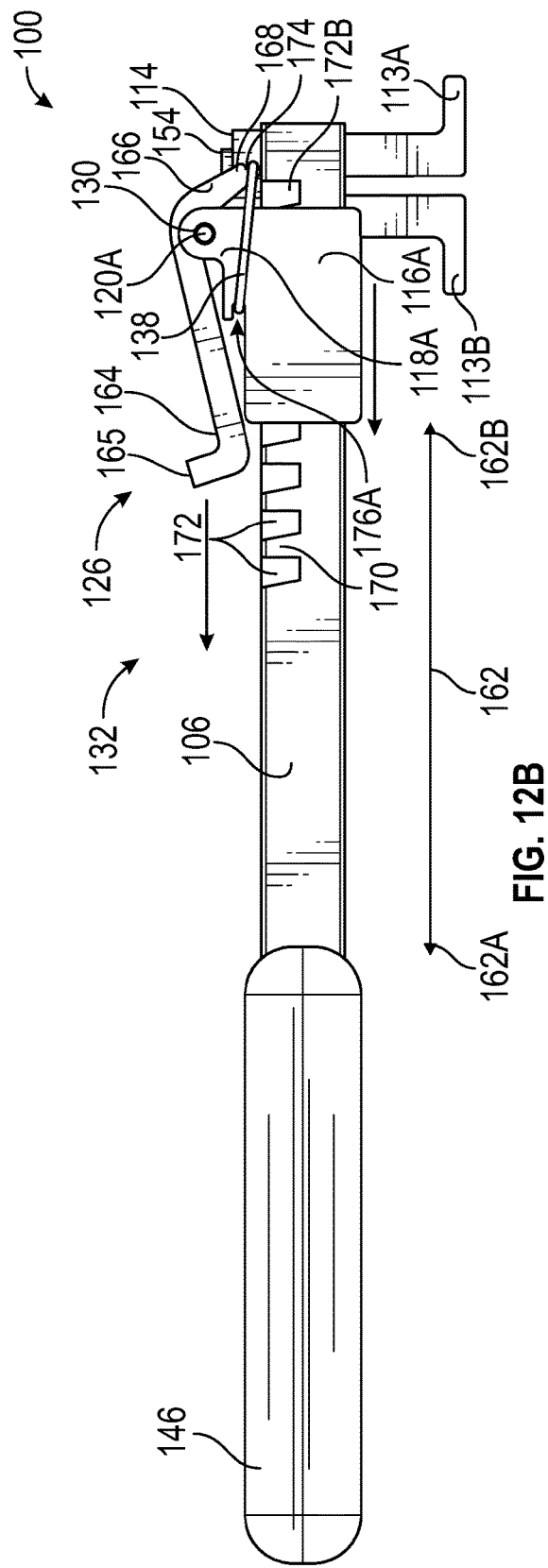
FIG. 12A
FIG. 12B

NON-METALLIC RETRACTOR DEVICE WITH A RATCHET ARM

FIELD

The present disclosure generally relates to surgical instruments, and in particular relates to an improved retractor device configured to retract incisions on a subject's body and retain catheters or shunt tubing in place during surgical procedures.

BACKGROUND

Certain surgical procedures require retraction of soft tissue and a shunt to remove bodily fluids. Hydrocephalus, for example, is a condition caused by buildup of excess cerebrospinal fluid (CSF) in the ventricles of the brain. The increased size of the ventricles causes excess pressure on brain tissue. Symptoms may vary with age, disease progression, and individual differences, but in some cases may be fairly severe and lead to seizures, mental impairment, or death.

A common procedure to address this condition involves the formation of a surgical incision to access the excess fluid. The incision may be held open by a locking retractor tool such as a retractor device; however, conventional retractor devices have various drawbacks. Retractor devices are generally reusable and costs for each device may range anywhere from $100 to $500; with significant further costs being incurred during sterilization and maintenance. Surgical retractors are commonly made from metals such as stainless steel or anodized aluminum.

To remove the excess CSF, the procedure may further include the placement of a ventriculoperitoneal (VP) shunt to drain the excess fluid from the brain into the abdomen, blood vessels, pleura, or a number of other potential spaces in the human body. The shunt may include a ventricular catheter that is inserted into one of the brain's ventricles with a portion of the catheter remaining extracranial. This catheter is typically referred to as the proximal catheter. The extracranial end of the proximal catheter is typically attached to an adjustable valve that regulates the flow of fluid out of the ventricles. The shunt also includes a distal catheter that most often drains into the peritoneal space. This catheter is connected to the distal end of the valve, is tunneled underneath the skin, and drains into the abdomen where the fluid is then reabsorbed. During surgical placement of the proximal catheter, the intracranial pressure and/or gravity can cause this catheter to move into or out of the brain. There is also a risk of overdraining the ventricles once the proximal catheter is placed, requiring occlusion of the extracranial end of the catheter until it is connected to the inlet port of the valve.

Electromagnetic navigation guidance systems (EM systems) are often used throughout the same procedure to ensure correct placement of the proximal catheter into one of the brain's ventricles. EM systems rely upon magnetic fields to relay information to the surgeon about where in space certain surgical instruments, such as stylets inserted through the proximal catheter, are positioned in relation to the patient. Yet, EM systems often malfunction when metallic materials are used in close proximity. Thus, conventional metal retractor devices can cause a loss of catheter visualization during the most crucial parts of the procedure. Further, as described herein, the proximal catheter may migrate in or out of the brain during the procedure, or overdrain the brain's CSF if not properly secured after intracranial placement.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

FIGS. 12A-12D are corresponding side views illustrating the sequences of FIGS. 11A-11D for engaging the retractor device of FIG. 1 from a closed configuration to an open configuration, according to aspects of the present disclosure.

DETAILED DESCRIPTION

Figure 1:
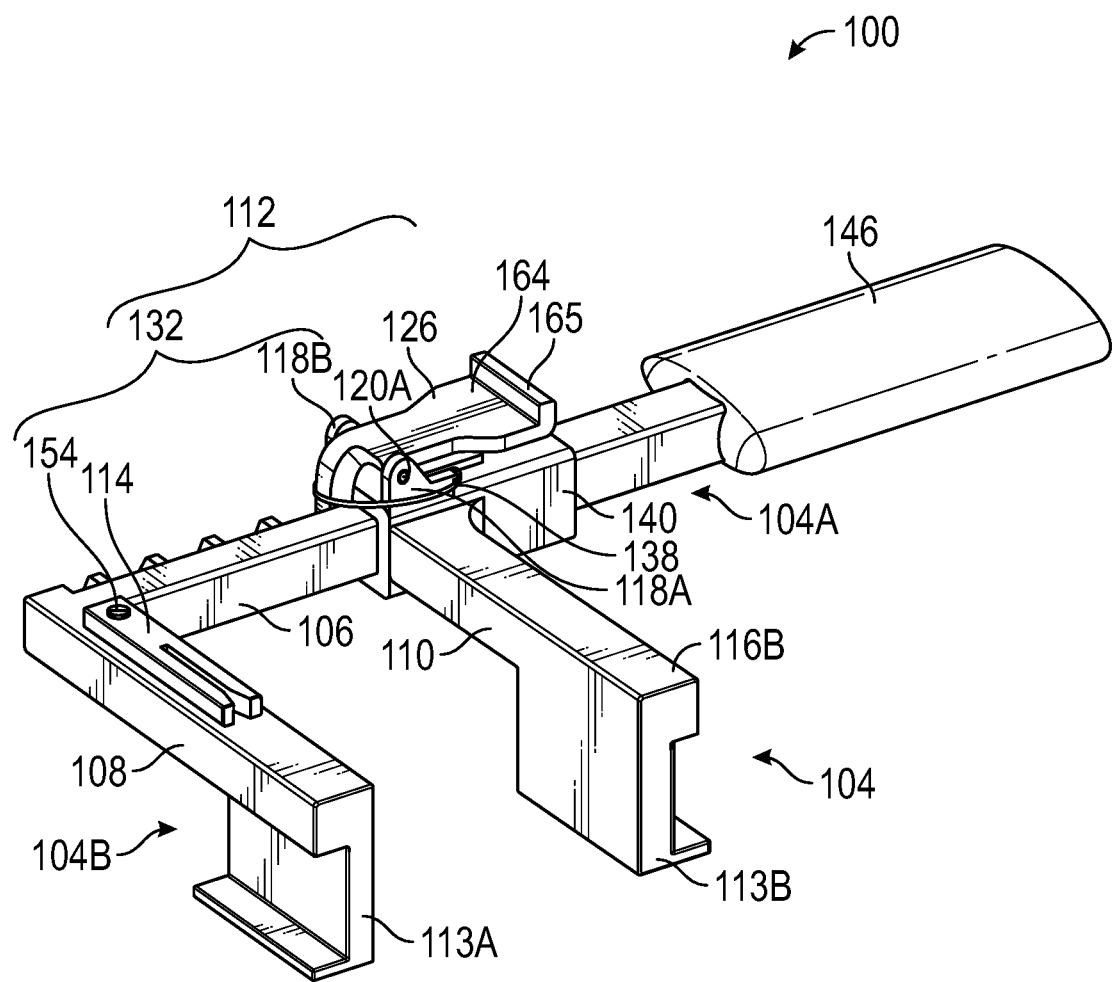
FIG. 1 is a perspective view of a system for retracting an incision and retaining a shunt in place including a retractor device, according to aspects of the present disclosure.

Various embodiments of a retracting device for retracting an incision and retaining a shunt or other tubing are described herein. In some embodiments, the retractor device defines a retractor body having a first segment and a second segment oriented in perpendicular relation relative to the first segment. The retractor device may further include an arm in sliding engagement along the first segment of the retractor body. The retractor device may further include a ratchet assembly defining a linear rack portion formed along a portion of the first segment of the retractor body. In addition, the ratchet assembly may define a pawl portion of a button mounted to the arm and in operative engagement with a locking mechanism that forcibly biases the pawl portion of the button along the rack portion. The ratchet assembly is configured to control the linear sliding movement of the arm along the first segment of the retractor body to retract an incision as described herein. In some embodiments, the retractor device is manufactured entirely from a non-metallic material such as a glass fiber composite. In some embodiments, a shunt retainer may be coupled to the retractor device along the retractor body for controlling movement of a catheter or shunt tubing during surgery. Referring to the drawings, one embodiment for an improved retractor device for retracting an incision and retaining a shunt is illustrated and generally indicated as 100 in FIGS. 1-15, 17, 20, and 21.

Referring to FIGS. 1-8, the retractor device 100 is configured to retract an incision along the skin, muscle, or other bodily tissues or combinations thereof, as described herein. The retractor device 100 includes a retractor body 104 having a first segment 106 defined along a proximal portion 104A of the retractor body 104 and a second segment 108 defined along a distal portion 104B of the retractor body 104 and in communication with the first segment 106. As shown, the first segment 106 may be in perpendicular relation with the second segment 108 such that a right angle is defined at the intersection between the first segment 106 and the second segment 108.

The retractor device 100 further includes an arm 110 in sliding engagement along the first segment 106 of the retractor body 104 and oriented in parallel relation relative to the second segment 108 of the retractor body 104. A ratchet assembly 112 defined along the first segment 106 controls the sliding engagement of the arm 110 along the first segment 106, as further described herein. As further shown, a first retracting end 113A may be defined along the second segment 108 of the retractor body 104, and a second retracting end 113B may be defined along a portion of the arm 110 such that the second retracting end 113B is oriented in parallel relation relative to the first retracting end 113A. The ratchet assembly 112 may be actuated to control movement of the arm 110 and the second retracting end 113B away from the first retracting end 113A to retract an incision, as further described herein. As shown in FIGS. 1, 2, 3, 9-11, 16 and 17, in some embodiments, a shunt retainer 114 may be engaged (e.g., movably engaged) to the second segment 108 of the retractor body 104 for retaining a catheter, shunt tubing, or any other surgical implement as needed, as described in greater detail below.

Referring to FIGS. 2-8, the arm 110 of the retractor device 100 may define a shoulder portion 116A and an elongated portion 116B with the second retracting end 113B defined along the elongated portion 116B of the arm 110. In some embodiments, the shoulder portion 116A of the arm 110 may define a first and second mounts 118A and 118B oriented in parallel relation along the shoulder portion 116B as illustrated. The first mount 118A may define an aperture 120A and the second mount 118B may define an aperture 120B such that the apertures 120A and 120B are linearly aligned along a common horizontal axis.

Figure 2:
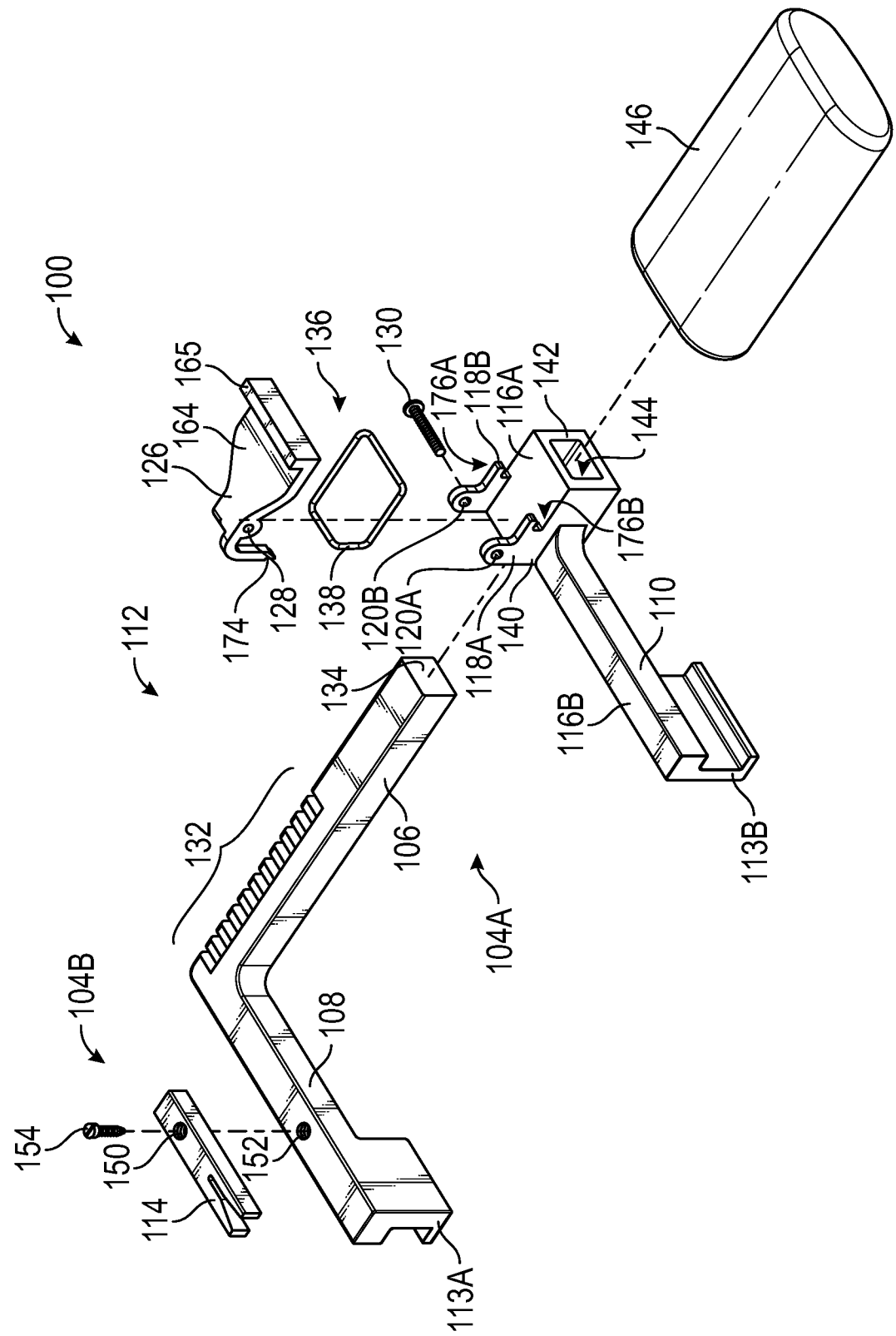
FIG. 2 is an exploded view of the retractor device of FIG. 1, according to aspects of the present disclosure.
Figure 3:
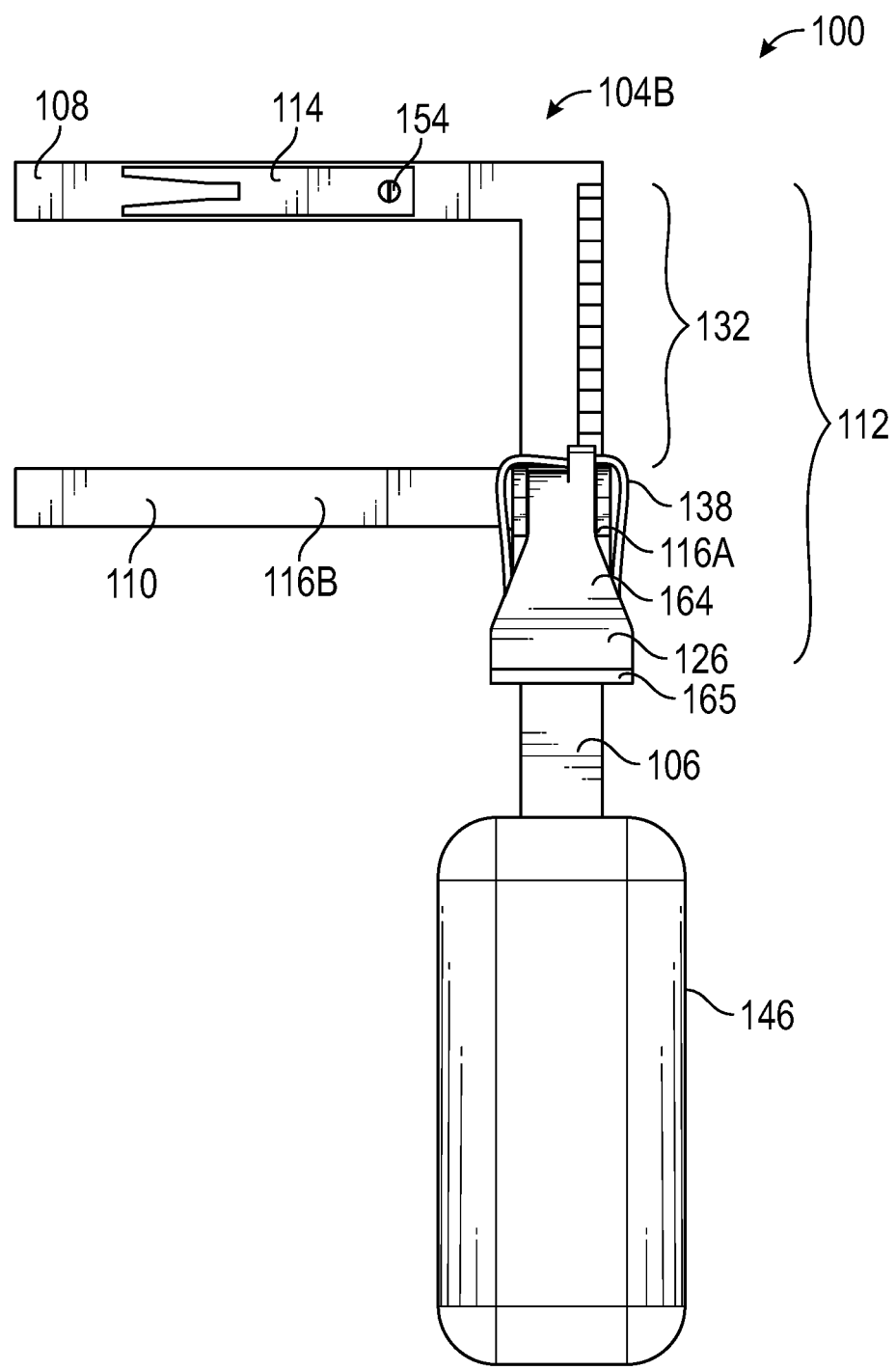
FIG. 3 is a front view of the retractor device of FIG. 1, according to aspects of the present disclosure.
Figure 4:
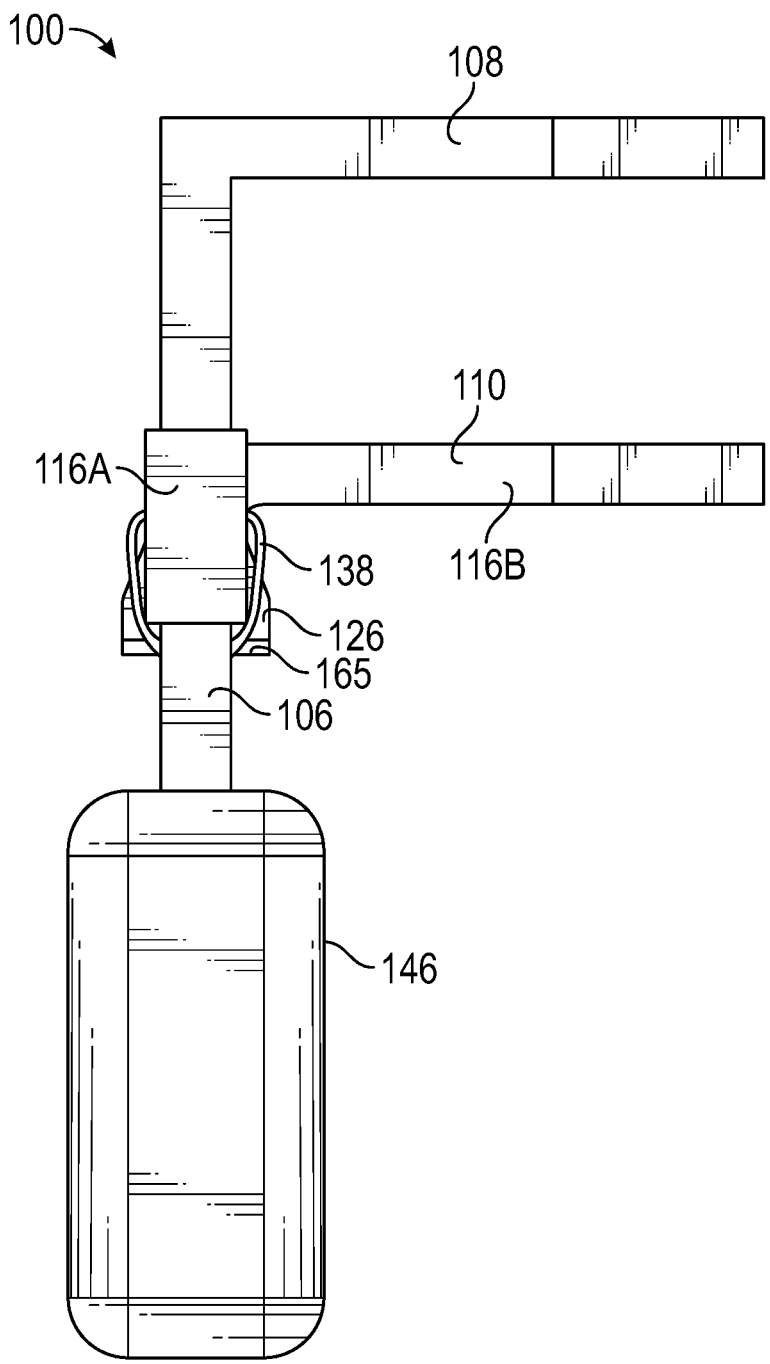
FIG. 4 is a rear view of the retractor device of FIG. 1, according to aspects of the present disclosure.
Figure 5:
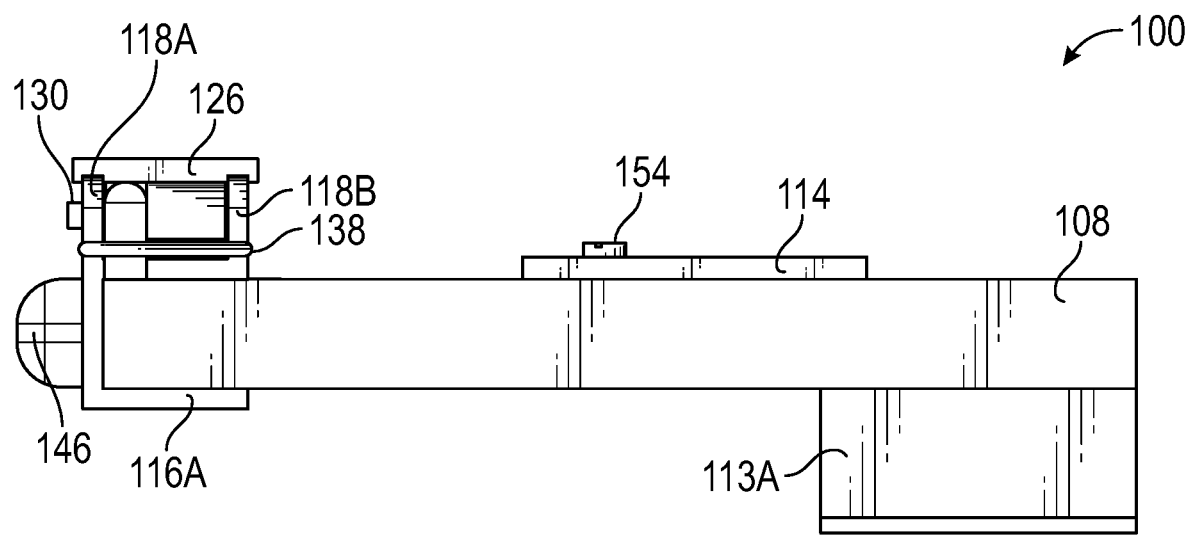
FIG. 5 is a top view of the retractor device of FIG. 1, according to aspects of the present disclosure.
Figure 6:
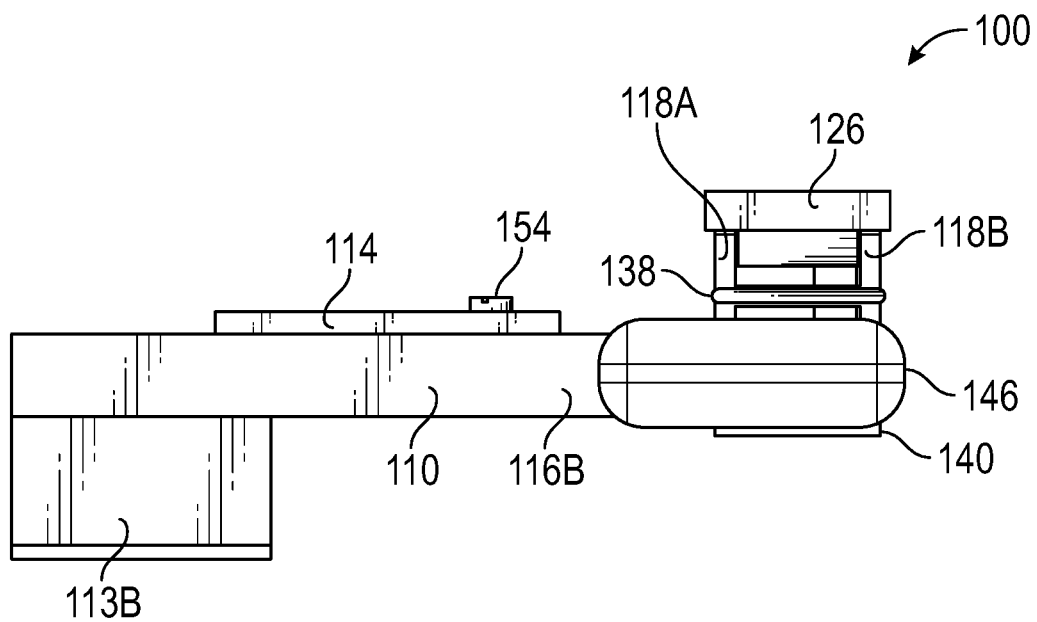
FIG. 6 is a bottom view of the retractor device of FIG. 1, according to aspects of the present disclosure.
Figure 7:
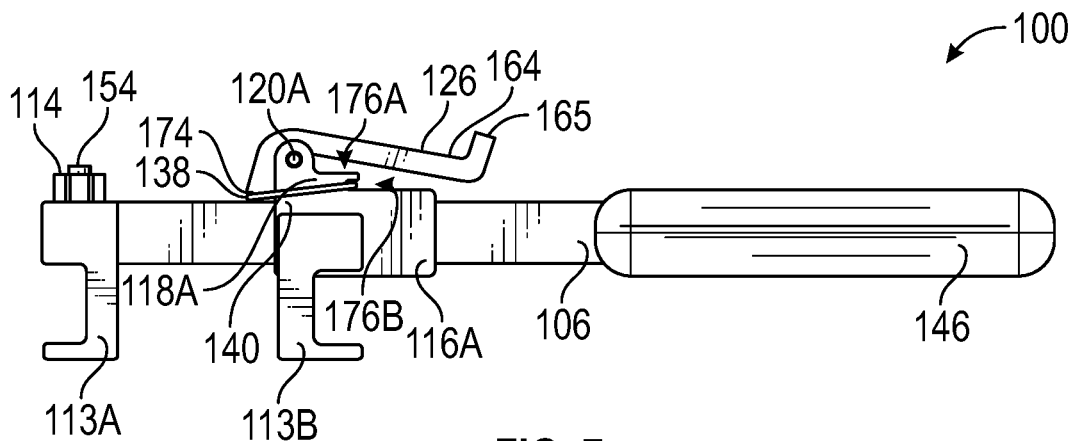
FIG. 7 is a first side view of the retractor device of FIG. 1, according to aspects of the present disclosure.
Figure 8:
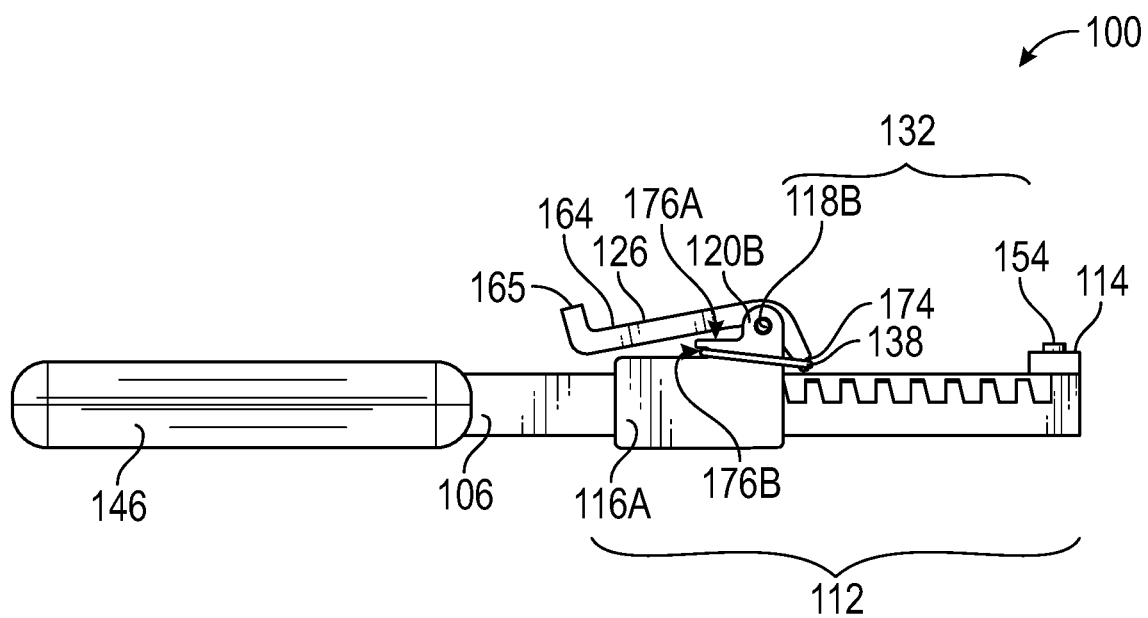
FIG. 8 is a second side view of the retractor device of FIG. 1, according to aspects of the present disclosure.

Referring to FIG. 2, in some embodiments a button 126 may be positioned between the first mount 118A and the second mount 118B for positioning the arm 110 along the ratchet assembly 112. In some embodiments, an opening 128 may be defined through a center portion of the button 126 that is aligned (e.g., linearly aligned) with the aperture 120A and aperture 120B of the first and second mounts 118A and 118B. A securing member 130, such as a non-metal nylon pivot pin, or nylon screw, may be extended through the aperture 120A, the opening 128, and the aperture 120B to mount the button 126 to the first and second mounts 118A and 118B in a fixed relationship relative to the shoulder portion 116A of the arm 110, as depicted in FIG. 2. In this manner, the button 126 is movable about the securing member 130.

In addition, the retractor device 100 includes a rack portion 132 defined along the first segment 106 of the retractor body 104. In operation, the button 126 engages with the rack portion 132 as part of the ratchet assembly 112 to lock the arm 110 in a stationary position relative to the first segment 106 of the retractor body 104, as further described herein. The rack portion 132 may define a predetermined length formed along the first segment 106 of the retractor body 104 and this predetermined length may vary depending upon the degree of retraction desired for the retracting device 100. In some embodiments, the rack portion 132 commences or extends from the intersection of the first segment 106 and the second segment 108 of the retractor body 104 and terminates before a free end 134 of the retractor body 104 defined along the first segment 106. In some embodiments, the rack portion 132 may be formed partially within a width of the first segment 106 of the retractor body 104, although the present disclosure is not limited in this regard. The retractor device 100 may include a locking mechanism 136. In particular, the locking mechanism 136 includes a flexible member 138, such as an orthodontic rubber band, for biasing the button 126 into a locked position relative to the rack portion 132 and the shoulder portion 116A of the arm 110 as described below.

As further shown, the shoulder portion 116A of the arm 110 defines a first end 140 and a second end 142 formed opposite the first end 140 of the shoulder portion 116A. A channel 144 may be defined through the shoulder portion 116A from the first end 140 to the second end 142 and may be in perpendicular relation relative to the elongated portion 116B of the arm 110. The free end 134 of the retractor body 104 may be oriented towards the channel 144 and the first segment 106 of the retractor body 104 may be at least partially threaded or passed through the channel 144 of the shoulder portion 116A of the arm 110 to slideably engage the arm 110 along the first segment 106 of the retractor body 104; for example, to position the arm 110 in sliding engagement along the first segment 106 of the retractor body 104.

In some embodiments, the retractor device 100 includes a handle 146 for providing a gripping surface to a user. In some embodiments, the free end 134 of the retractor body 104 may be passed entirely through the channel 144 and mounted to the handle 146 of the retractor device 100 as indicated. In some embodiments, the free end 134 of the first segment 106 may be received within an opening (not shown) formed partially through the handle 146, and a securing mechanism (not shown), such as an adhesive, non-metal pin, screw, or nail, may be implemented to at least semi-permanently join the free end 134 of the first segment 106 of the retractor body 104 to the handle 146. The handle 146 may be formed of a shape that contours or otherwise accommodates the hand of a surgeon; in particular, the handle 146 allows a sole hand of a surgeon to grip the handle 146 and apply retraction to an incision using the sole hand, as further described herein. In some embodiments, the handle 146 may define curved edges, may be substantially rectangular in shape, and may be removable from the retractor body 104 in order to replace the handle 146 with an alternate handle of larger size or having a different shape. Further, although not depicted, the handle 146 may include a series of depressions that reflect the anatomical configuration of the user's hands so that the device may be held comfortably for extended periods of time.

As noted above, the shunt retainer 114 may be movably coupled (e.g., rotatably coupled) to the retractor body 104 and configured to engage and retain tubing, such as a catheter or shunt tubing, in a fixed stationary position relative to the retractor device 100. In some embodiments, the shunt retainer 114 is rotatably coupled to the retractor body 104 by a securing member 154 inserted through an opening 150 of the shunt retainer 114 and opening 152 the retractor body 104 that is aligned with opening 150. In some embodiments, the securing member 154 may be a non-metal nylon pin, screw, or the like. The shunt retainer 114 may be oriented by moving (e.g., rotating) the shunt retainer 114 about the securing member 154 to the desired orientation. It should be understood that the shunt retainer 114 may be similarly positioned along different locations of the retractor body 104 or other portions of the retractor device 100 as desired. The particular structure and configuration of the shunt retainer 114 will be discussed in greater detail below.

The retractor device 100 of the present inventive concept may be manufactured entirely from a non-metal material, or combinations thereof such as a plastic, rubber, nylon, glass fiber, a polymer-based biocompatible material, a bioactive material, a resin, ceramic composites, any material that does not cause interference with EM-guidance systems, or any combinations thereof. In some embodiments, materials used to form the retractor device 100 may include polymers such as Ixef® polyacrylamide (PARA), AvaSpire® polyaryletherketone (PAEK), and may include Acrylonitrile butadiene styrene (ABS). Because the retractor device 100 is made from such non-metal materials, the retractor device 100 reduces or avoids interference with EM systems. The retractor device 100 is further biocompatible and reduces the chance of inflicting harm around an incision or causing inflammation. In addition, the retractor device 100 is much lighter in weight as compared with conventional metallic retractors, is cheaper to manufacture, is disposable, and meets predefined mechanical engineering requirements and preferred surgical specifications, as further described herein. In one embodiment, a PARA 50% glass fiber composite may be utilized for manufacturing the retractor device 100, which accommodates surgical biomedical environments, and is structurally sufficient for the desired retraction operations described herein.

Figure 9:
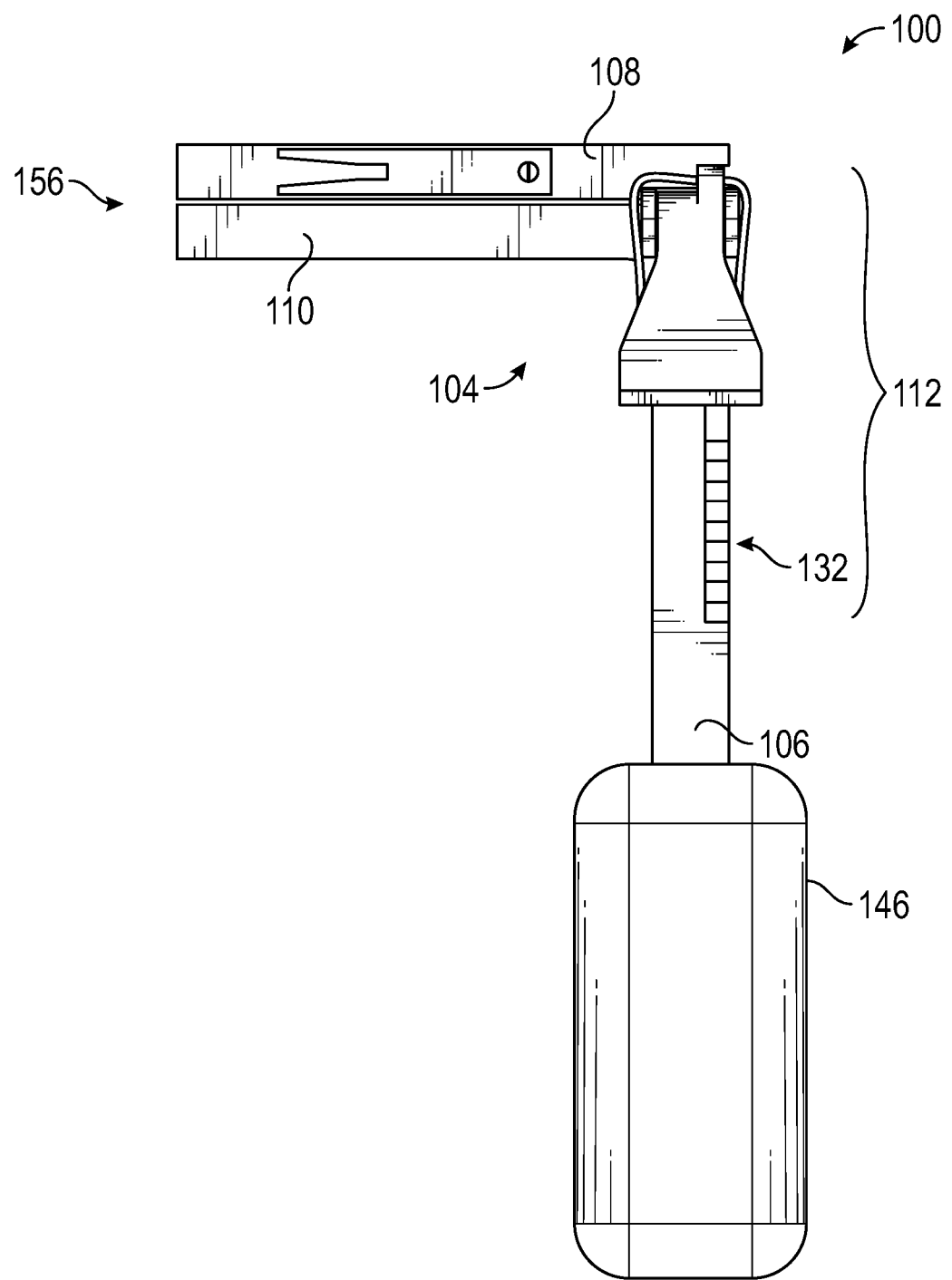
FIG. 9 is a front view of the retractor device of FIG. 1 shown in a closed configuration, according to aspects of the present disclosure.
Figure 10:
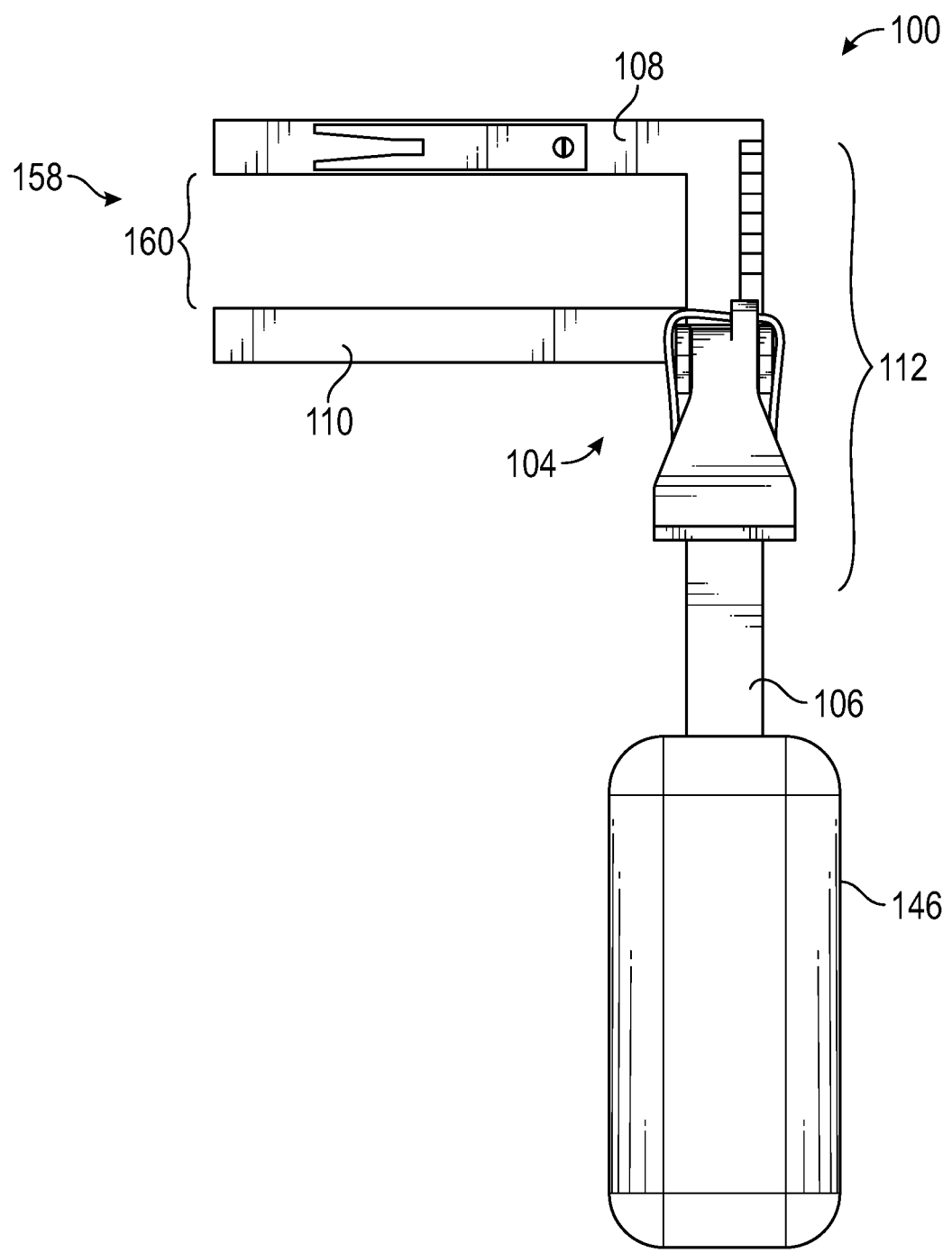
FIG. 10 is a front view of the retractor device of FIG. 1 shown in an open configuration, according to aspects of the present disclosure.

Referring to FIGS. 9-10, the arm 110 of the retractor device 100 may be oriented in different positions relative to the second segment 108 of the retractor body 104 to form a closed configuration, or an open configuration of the retractor device 100, or any position between the closed and open positions, using the ratchet assembly 112. For example, in FIG. 9, a user, e.g. a surgeon, may engage the ratchet assembly 112 to slide the arm 110 along the first segment 106 away from the handle 146 until the arm 110 is aligned along the second segment 108 of the retractor body 104 to form a closed configuration 156 of the retractor device 100. As shown in FIG. 10, the user may also engage the ratchet assembly 112 to slide the arm 110 along the first segment 106 to a predetermined distance away from the second segment 108 of the retractor body 104 to form an open configuration 158 of the retractor device 100. In one embodiment, the open configuration 158 defines a retraction distance 160, i.e., the distance between the arm 110 and the second segment 108 of the retractor body 104, which may generally range within approximately zero to three inches. However, the dimensions of the various components of the retractor device 100 may be adjusted as needed to accommodate greater retraction ranges as desired.

Referring to FIGS. 11A-11D, and 12A-12O, greater detail regarding the ratchet assembly 112 is illustrated. Using the ratchet assembly 112, the arm 110 is configured for movement and locking or self-retention at predefined locations along an axis 162 defined along the first segment 106 of the retractor body 104 with the axis 162 defining a forward direction 162A and a reverse direction 162B. The ratchet assembly 112 may be collectively defined by the button 126, which is rotatable axially about the securing member 130, and the rack portion 132. In some embodiments, a first end of the button 126 defines a paddle portion 164, which may include a lip 165 and a second end of the button 126 opposite the first end defines a pawl portion 166 which defines a tip 168 or detent configured to engage with the rack portion 132 defined along the first segment 106 of the retractor body 104.

As further shown, the rack portion 132 may be a linear rack defining an array of ratchet teeth 170 extending along the axis 162 of the first segment 106. In some embodiments, the array of ratchet teeth 170 may be formed within a profile or vertical footprint of the first segment 106 of the retractor body 104 so that the arm 110 may slide freely along the first segment 106 of the retractor body 104 over the rack portion 132. The rack portion 132 may further define a plurality of slots 172 in which a respective slot is juxtapositioned between a respective pair of ratchet teeth 170. The tip 168 of the pawl portion 166 may be positioned within one of the plurality of slots 172 to lock or to self-retain the arm 110 in a stationary position relative to the second segment 108 of the retractor body 104, as further described herein. In some embodiments, the slots 172 may be spaced apart at about or around 0.2 inch increments to provide ample retraction adjustment resolution. In some embodiments, each of the slots 172 may be angled or define angled slots. More specifically, each of slots 172 may have a generally right-triangle shaped configuration as shown to restrict or prevent movement of the arm 110 and the tip 168 of the pawl portion 166 in the reverse direction 162B when the tip 168 is engaged within one of the plurality of slots 172, thereby maintaining some degree of retraction during surgery. It should be appreciated that the slots 172 of the rack portion 132 may vary with respect to shape, amount, and size of ratchet teeth 170 and slots 172 to accommodate different embodiments and the present inventive concept is not limited to the embodiments depicted.

Figure 11A:
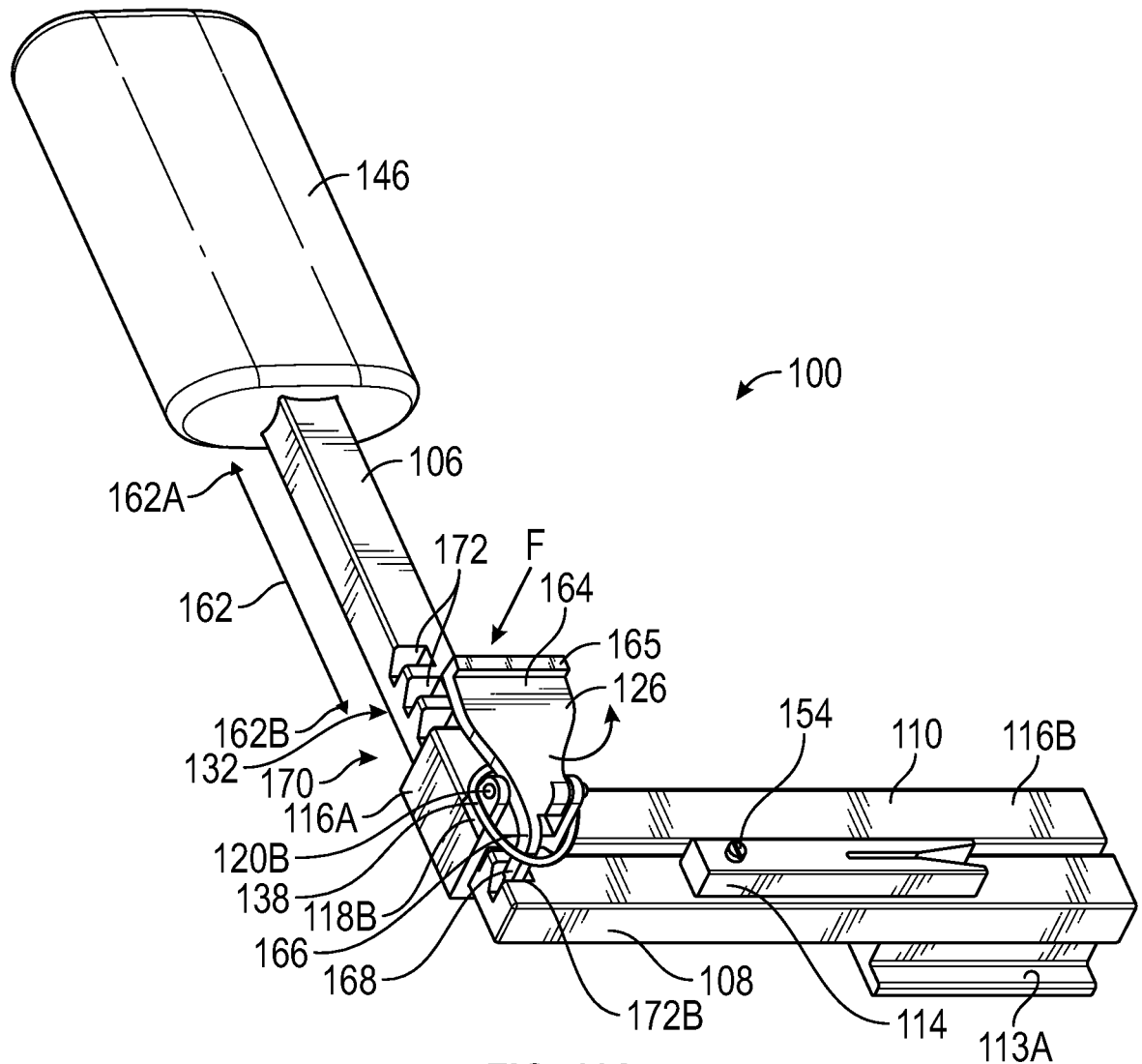
FIGS. 11A-11D are perspective views illustrating different sequences for engaging the retractor device of FIG. 1 from a closed configuration to an open configuration, according to aspects of the present disclosure.
Figure 12C:
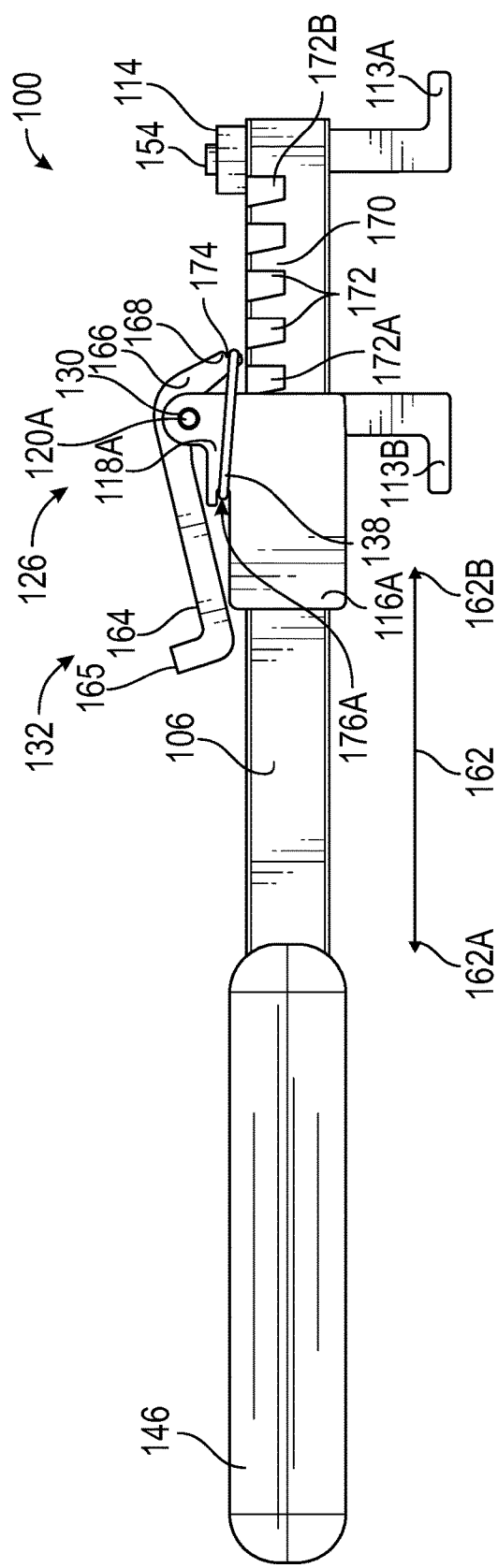

As further illustrated in FIGS. 12A-12D, a groove 174 may be defined along the pawl portion 166 of the button 126 between the tip 168 and the paddle portion 164. In addition, a groove 176A may be also be defined along the shoulder portion 116A below the first mount 118A and another groove 176B (FIG. 2) defined along the shoulder portion 116A below the second mount 118B. The groove 174, the groove 176A, and the groove 176B may define engagement points (not shown) for lateral engagement with the flexible member 138. More specifically, in some embodiments the flexible member 138 may be stretched and wrapped around the shoulder portion 116A along the groove 176A and the groove 176B, and may also be wrapped around the groove 174 in the manner shown. In this arrangement, the flexible member 138 applies tension or a bias to the button 126 along the groove 174 which generates a degree of clockwise axial force to the button 126 relative to the securing member 130. This clockwise axial force tends to maintain the tip 168 in a downward position such that the tip 168 is oriented towards the first segment 106 of the retractor body 104. Further, in this downward orientation, the tip 168 generally rests within one of the slots 172 which creates resistance to movement of the arm 110 along the first segment 106 of the retractor body 104. In other words, the tip 168 of the pawl portion 166 is forcibly biased within one of the plurality of slots 172 by the tension of the flexible member 138 as applied to the button 126 along the groove 174. Referring to FIG. 11A and FIG. 12A, in the closed configuration 156 the tip 168 may be positioned within the groove 172B.

Figure 11B:
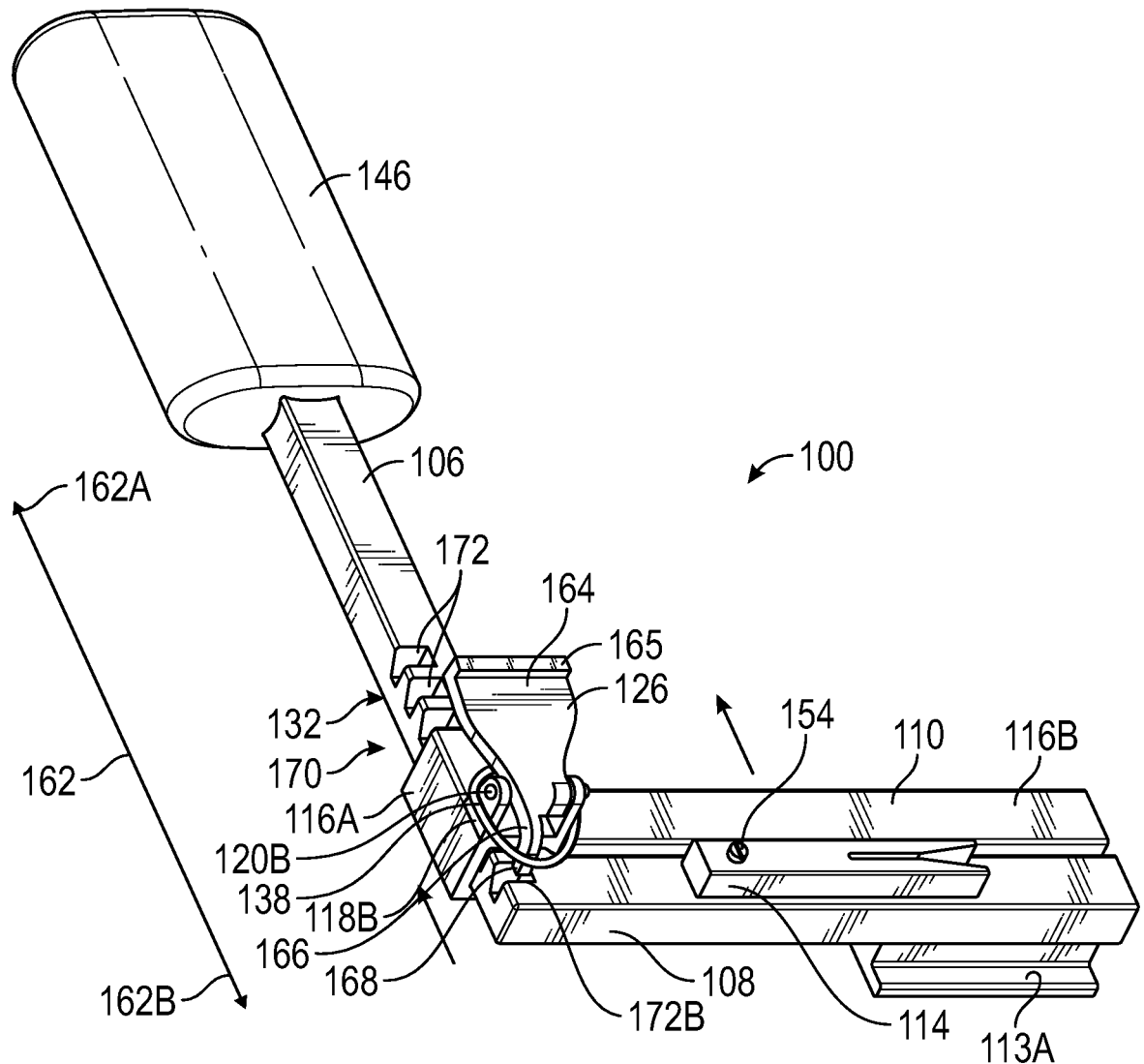
Figure 11C:
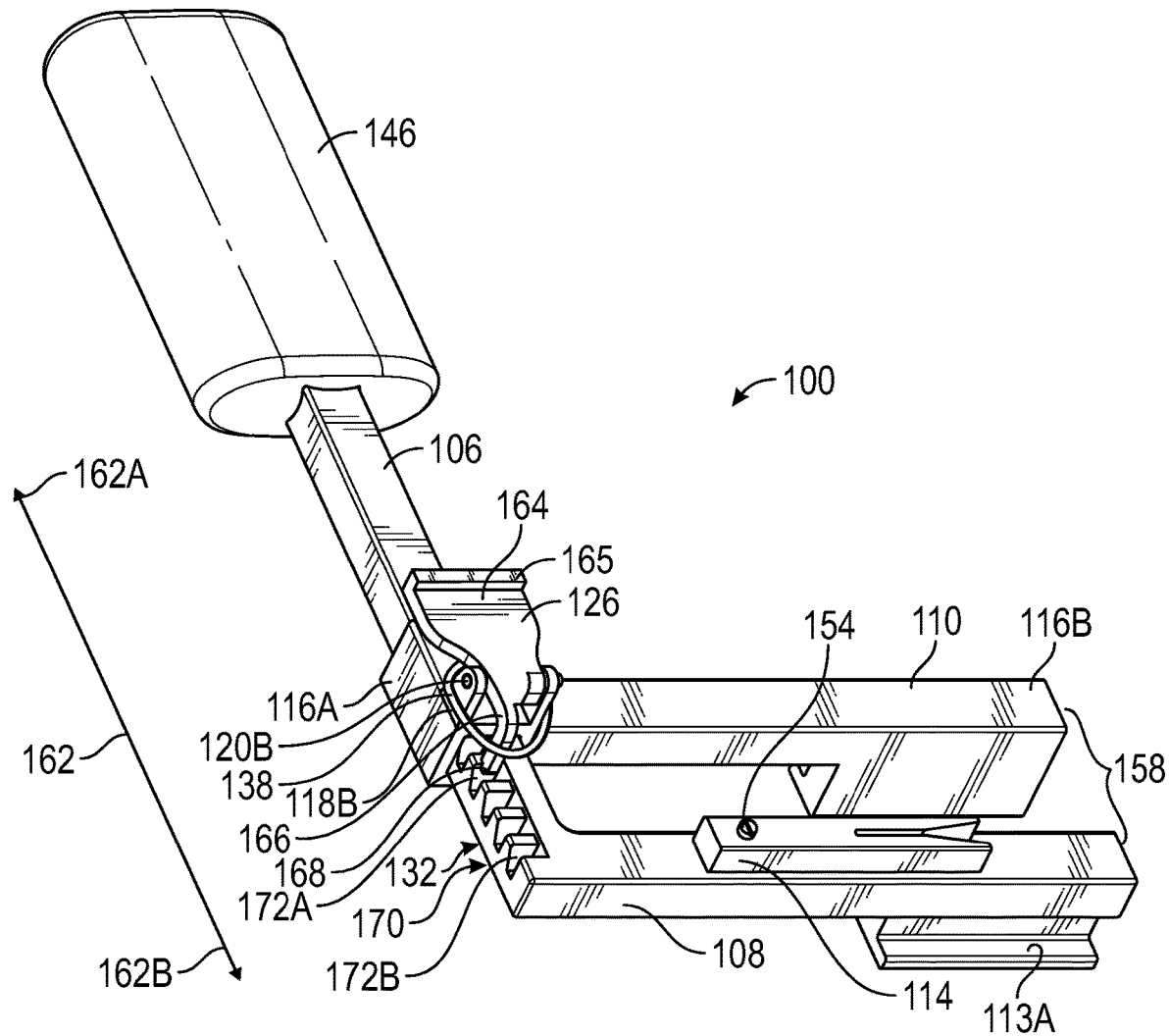

Referring to FIG. 11B and FIG. 12B, using a thumb or other body portion of a user, a downward force may be applied to the paddle portion 164 to stretch the flexible member 138, and axially rotate the paddle portion 164 of the button 126 about the securing member 130 in a counter clockwise direction towards the first segment 106 of the retractor body 104. Such axial rotation of the paddle portion 164 of the button 126 rotates the tip 168 of the pawl portion 166 outside of the rack portion 132 and the plurality of slots 172, thereby releasing the tip 168 of the pawl portion 166 from within the plurality of slots 172. Referring to FIG. 11C and FIG. 12C, so long as the button 126 remains depressed such that the tip 168 of the pawl portion 166 is temporarily released from within the plurality of ratchet slots 172, the arm 110 may slide freely along the first segment 106 of the retractor body 104 as desired. For example, the tip 168 may be released from the slot 172B, and the arm 110 may be moved along the first segment 106 to a position where the tip 168 is oriented over a slot 172A of the plurality of slots 172.

Figure 11D:
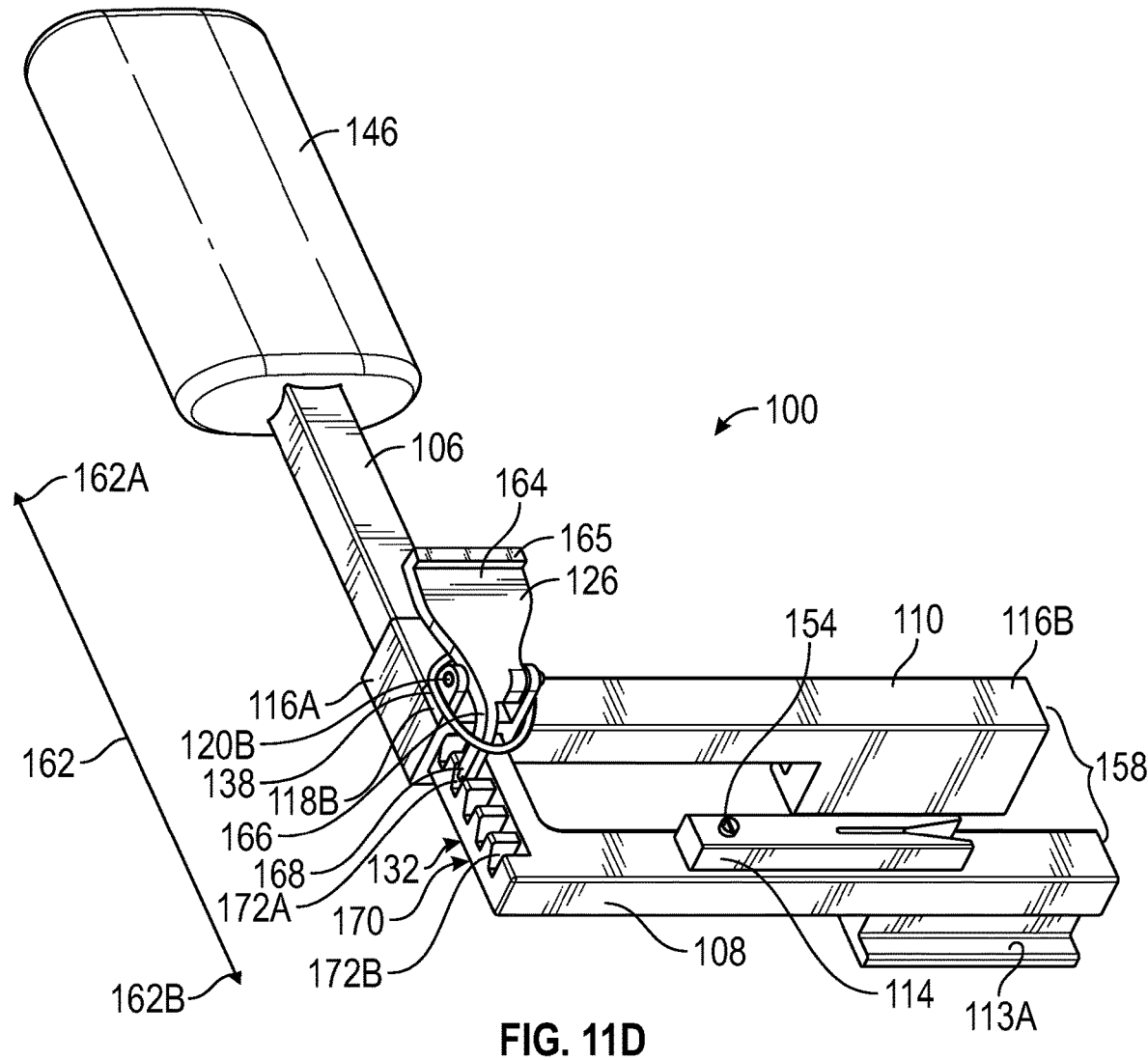
Figure 12D:
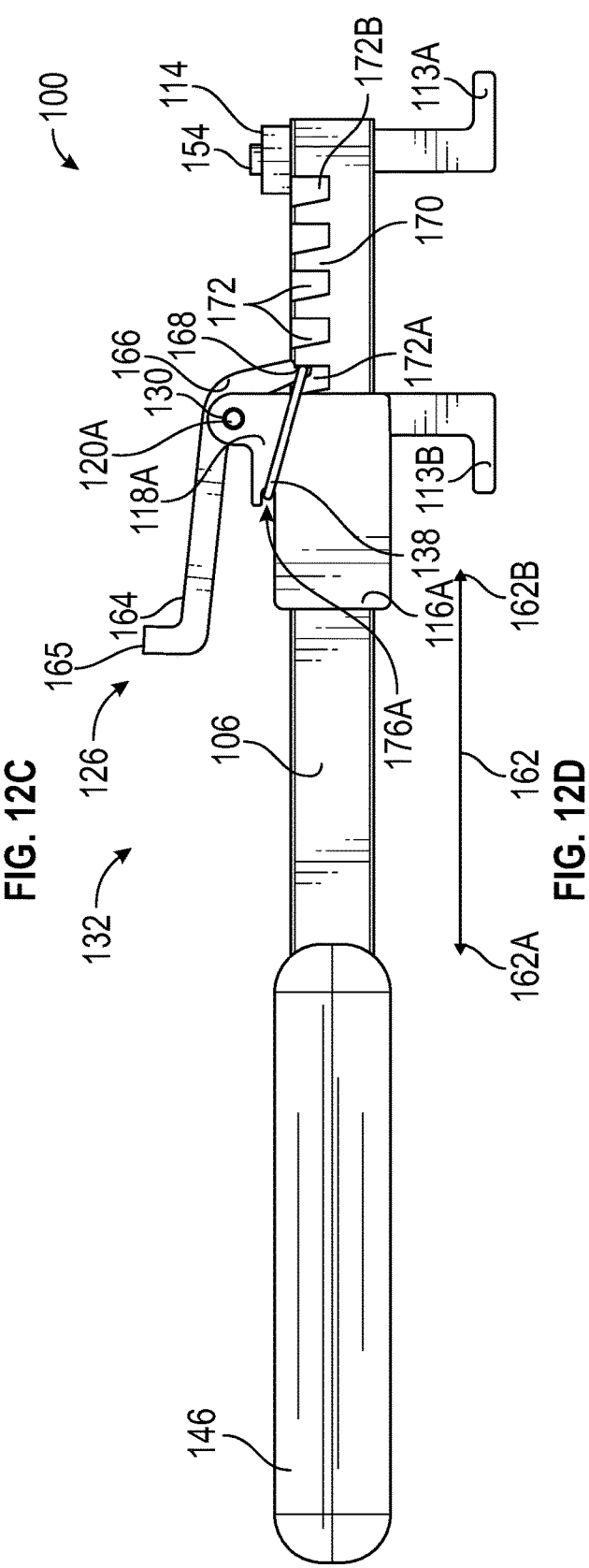

Referring to FIG. 11D and FIG. 12D, once the button 126 is no longer depressed or otherwise actuated, the tension and the associated clockwise axial force from the flexible member 138 causes the button 126 to rotate axially back about the securing member 130 in the clockwise direction. Such clockwise axial rotation of the button 126 rotates the tip 168 of the pawl portion 166 back down towards the rack portion 132 defined along the first segment 106 of the retractor body 104. In one embodiment of the open configuration 158, the tip 168 of the pawl portion 166 may be positioned within a slot 172A of the plurality of slots 172 once the button 126 is no longer actuated or depressed as described. Once the tip 168 is positioned within the groove 172A as shown, the arm 110 is locked in a stationary position, or retained, relative to the first segment 106 of the retractor body 104, restricting movement of the arm 110 at least in the reverse direction 162B.

Figure 13:
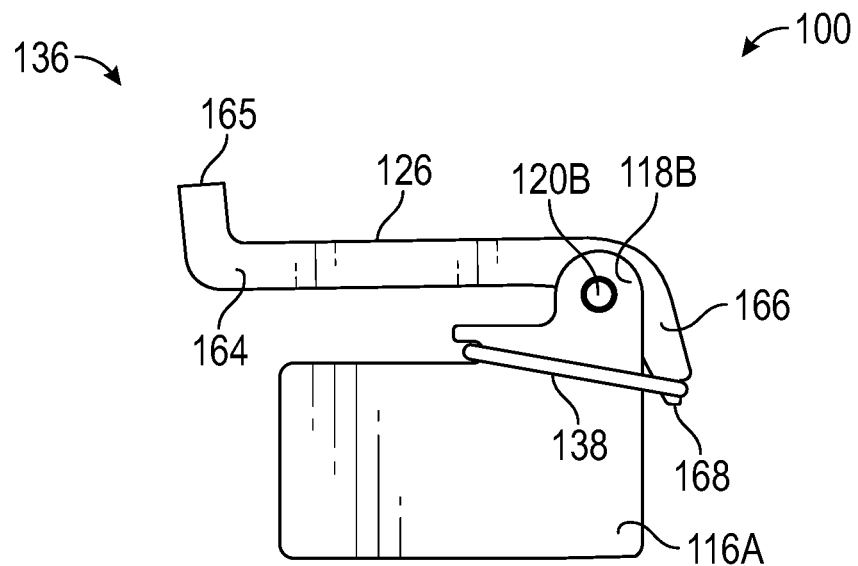
FIG. 13 is an enhanced side view of a first embodiment of a locking mechanism for engaging the retractor device of FIG. 1 from a closed configuration to an open configuration, according to aspects of the present disclosure.
Figure 14:
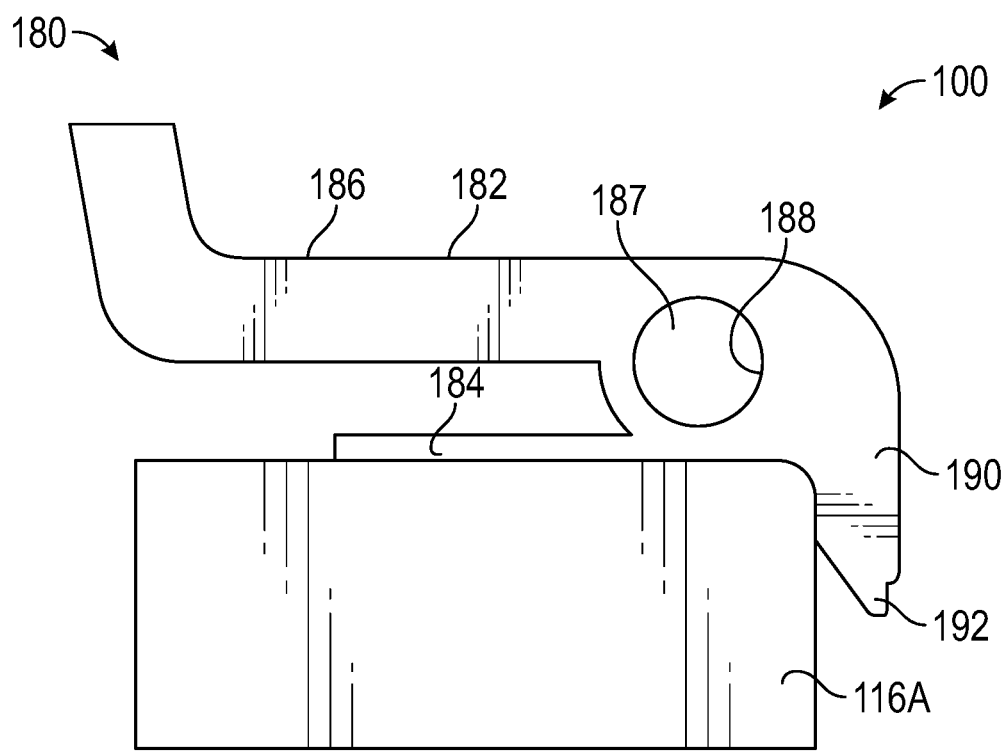
FIG. 14 is an enhanced side view of a second embodiment of a locking mechanism for engaging the retractor device of FIG. 1 from a closed configuration to an open configuration, according to aspects of the present disclosure.

Referring to FIG. 13, the locking mechanism 136 is defined by the dimensions of the button 126, and the implementation of the flexible member 138 along the button 126 as described, for biasing the tip 168 of the pawl portion 166 and temporarily locking the tip 168 within a respective slot of the plurality of slots 172 (FIGS. 11A-11D). In other words, using the locking mechanism 136 the tension forces applied by the flexible member 138 resets the pawl portion 166 and the tip 168 to within one of the slots 172 defined along the rack portion 132. Employing the flexible member 138 provides a low-cost and efficient method by exploiting the tension properties and elasticity of the flexible member 138 when the flexible member 138 is positioned along the button 126 as described herein. In some embodiments, the restoring force, or the bias applied by the flexible member 138 is approximately 2 to 3 lbs.

Other embodiments are contemplated for biasing the tip 168 of the pawl portion 166 within the plurality of slots 172. For example, referring to FIG. 14, another embodiment of a locking mechanism, designated 180, may define a button 182. The button 182 may define a shape similar to the button 126; however, the button 182 may include an extrusion 184 defined along a bottom portion of the button 182 as shown. More specifically, the extrusion 184 may comprise a member (e.g., a substantially linear planar member) extending in parallel below a paddle portion 186 of the button 182, which may be fixedly oriented along a portion of the shoulder portion 116A of the arm 110. The button 182 may be axially rotatable about a securing member 187 inserted through an opening 188 similar to opening 128. In addition, the button 182 may be mounted to the shoulder portion 116A along the first mount 118A and the second mount 118B similar to the button 126. The button 182 may further define a pawl portion 190 similar to the pawl portion 166 and a tip 192 similar to the tip 168. In this embodiment, the button 182, when depressed along the paddle portion 186, deflects downward along the extrusion 184, thereby temporarily moving the tip 192 of the pawl portion 190 in an upwards direction (not shown), which may temporarily release the tip 192 from one of the slots 172 of the rack portion 132 (in a manner similar to the embodiment illustrated in FIG. 2). The locking mechanism 180 relies upon a restoring force applied by elastic deflection of the paddle portion 186 of the button 182. As such, the button 182 may be manufactured using a flexible plastic or similar non-metallic material to allow ample predetermined deflection when a downward force is applied to the paddle portion 186 towards the extrusion 184.

Figure 15:
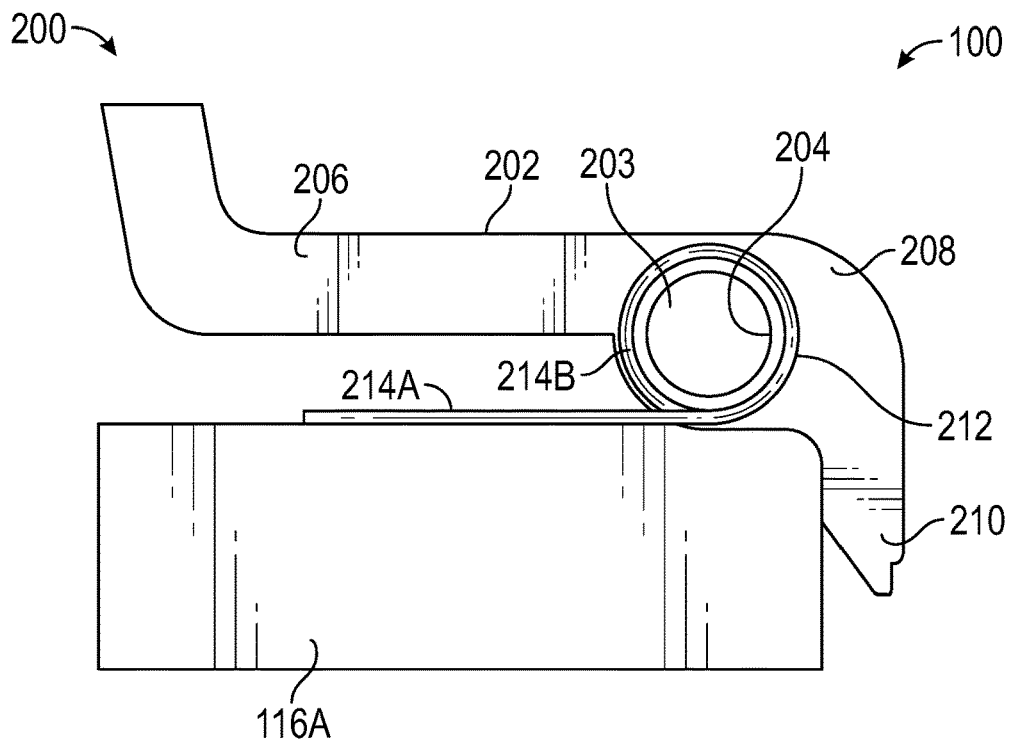
FIG. 15 is an enhanced side view of a third embodiment of a locking mechanism for engaging the retractor device of FIG. 1 from a closed configuration to an open configuration, according to aspects of the present disclosure.

Referring to FIG. 15, another embodiment of a locking mechanism 200, may define a button 202 similar to the button 126. The button 202 may be axially rotatable about a securing member 203 inserted through an opening 204 similar to the opening 128, and the button 202 may be mounted to the shoulder portion 116A along the first mount 118A and the second mount 118B similar to button 126. The button 202 may further define a paddle portion 206, a pawl portion 208, and a tip 210. In this embodiment, the button 202 of the locking mechanism 200 may include an embedded non-metallic (e.g., polymer-based) torsion spring 212. The embedded plastic torsion spring 212 may define a tail portion 214A extending beneath the paddle portion 206 which may be mounted to a surface of the shoulder portion 116A, and a coil portion 214B defined along the opening 204. Because the tail portion 214A of the embedded plastic torsion spring 212 is mounted to the shoulder portion 116A, depressing the button 202 along the paddle portion 206 causes temporary partial uncoiling of the coil portion 214B of the embedded torsion spring 212, thereby temporarily moving the tip 210 of the pawl portion 208 in an upwards direction, which may temporarily release the tip 210 from slots 172 of the rack portion 132 (not shown). Various embodiments are contemplated using non-metal materials. In other embodiments, a die spring or compression spring may be substituted for the torsion spring.

Figure 16:
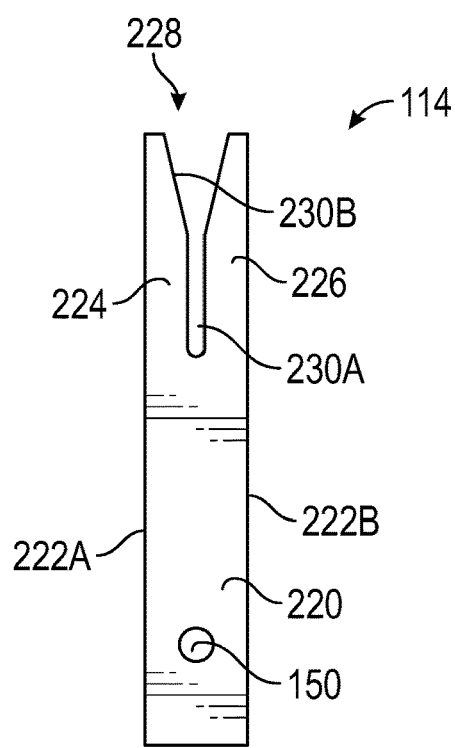
FIG. 16 is a front view of a first embodiment of a shunt retainer for use with the retractor device of FIG. 1, according to aspects of the present disclosure.

As described above, certain surgical procedures (such as ventriculoperitoneal shunt insertions and revision procedures) require the use of non-rigid and implantable catheters that divert fluid from one body space to either the external environment or to another body space. It is desirable to maintain a shunt in place during a procedure in order to resist movement of the shunt in and out of an incision. Referring to FIG. 16, one embodiment of the shunt retainer 114 discussed above is illustrated. As shown, the shunt retainer 114 may include the opening 150 for receiving the securing member 154 (FIG. 1) to engage the shunt retainer 114 along the retractor body 104. The shunt retainer 114 may be made from the same or similar non-metallic materials as the retractor device 100, described herein. As such, the shunt retainer 114 does not interfere with EM systems and may be implemented to maintain portions of a shunt in a stationary position relative to the retractor body 104 and the patient.

In the embodiment shown in FIG. 16, the shunt retainer 114 includes a base 220, defining a first lateral side 222A and a second lateral side 222B formed opposite the first lateral side of 222A. The shunt retainer 114 further defines a first member 224 extending from the first lateral side 222A of the base 220, and a second member 226 extending from the second lateral side 222B of the base 220. In some embodiments, the second member 226 is oriented in parallel relation relative to the first member 224 as shown. A Y-shaped channel 228 may be defined between the first member 224 and the second member 226 of the shunt retainer 114. In some embodiments, the Y-shaped channel 228 defines a proximal section 230A and a distal section 230B that is wider than the proximal section 230A. In the embodiment shown, the circular shape of the opening 150 formed along the shunt retainer 114 substantially corresponds to the circumference and shape of the securing member 154. Accordingly, the shunt retainer 114 is configured to pivot, rotate laterally, or otherwise move about a fixed point defined by the securing member 154 by virtue of the dimensions of the opening 150 as shown in FIG. 2.

Figure 17A:
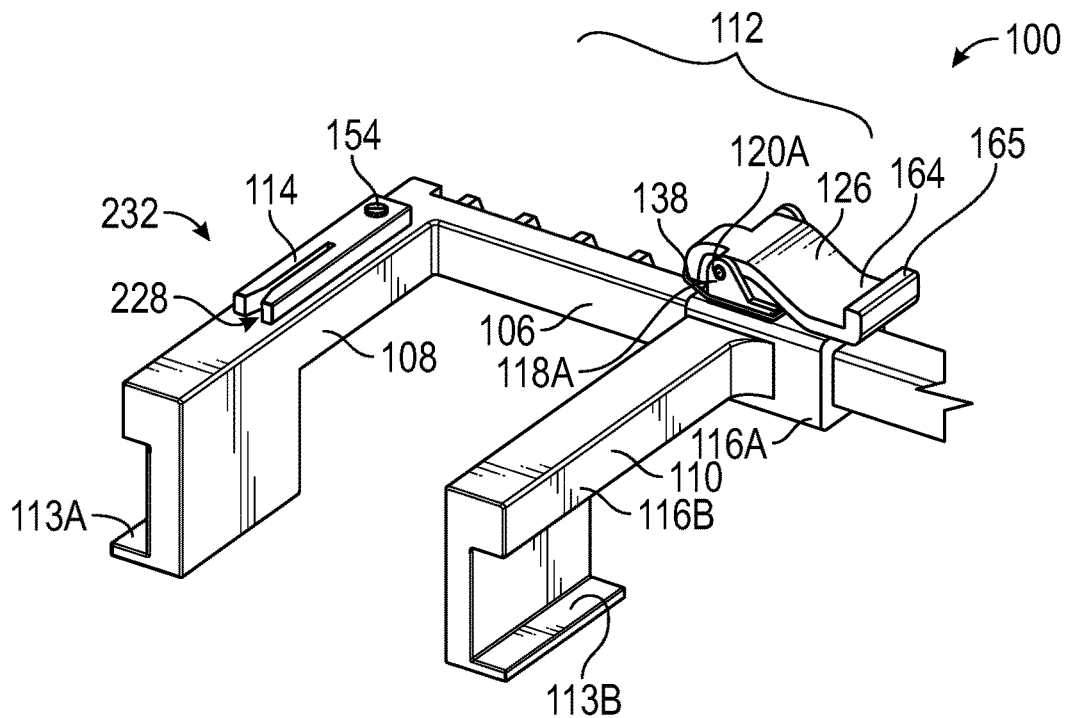
FIGS. 17A-17B illustrate different configurations of the shunt retainer along the retractor device of FIG. 1, according to aspects of the present disclosure.
Figure 17B:
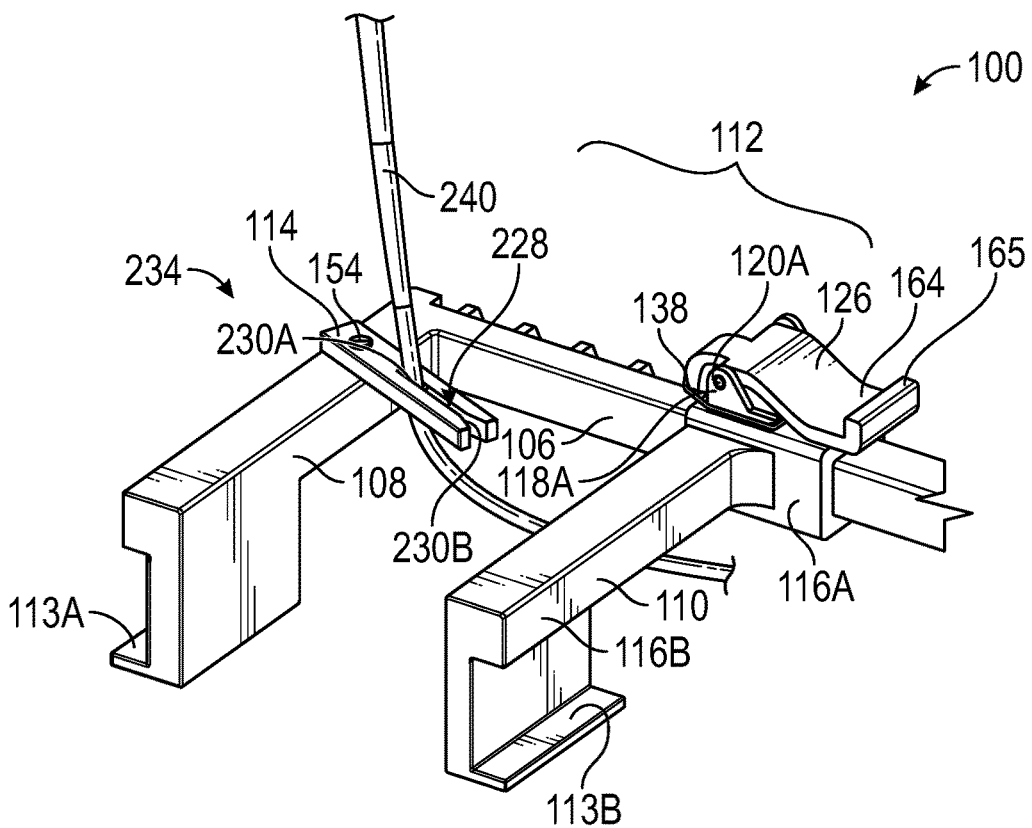

Referring to FIGS. 17A and 17B, the shunt retainer 114 may be rotated or may pivot laterally about the securing member 154 over the retractor body 104. When not in use, the shunt retainer 114 may be oriented in a first position 232 such that the shunt retainer 114 is nearly or completely entirely disposed over a footprint of the retractor body 104 for storage and protection as illustrated in FIG. 17A. As shown in FIG. 17B, the shunt retainer 114 may further be shifted to a second position 234 relative to the retractor body 104 such that a portion of the shunt retainer 114 extends outside a footprint of the retractor body 104. In this second position 234 (or in the first position 232 or otherwise), the shunt retainer 114 may engage with a shunt tubing 240 along the Y-shaped channel 228. Specifically, the shunt retainer 114 is configured to receive the shunt tubing 240 through the distal section 230B of the Y-shaped channel 228 and occlude the shunt tubing 240 when placed or positioned along the proximal section 230A of the Y-shaped channel 228.

Figure 18:
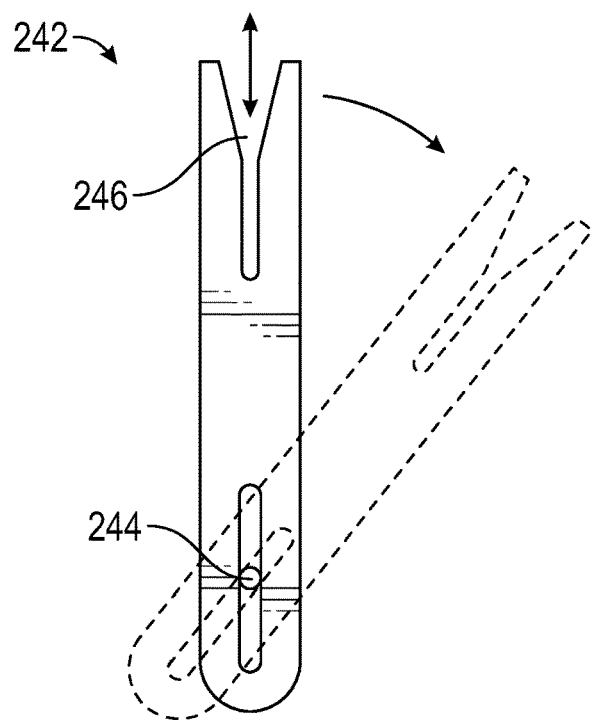
FIG. 18 is a front view of a second embodiment of a shunt retainer for use with the retractor device of FIG. 1, according to aspects of the present disclosure.
Figure 19:
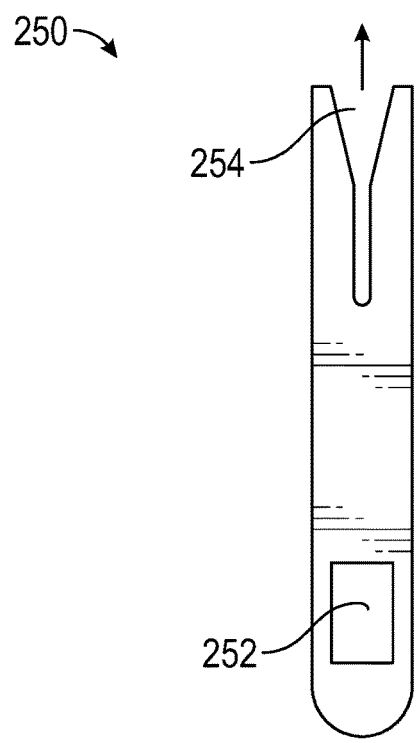
FIG. 19 is a front view of a third embodiment of a shunt retainer for use with the retractor device of FIG. 1, according to aspects of the present disclosure.

Referring to FIGS. 18 and 19, alternative embodiments of a shunt retainer are contemplated. For example, FIG. 18 shows a shunt retainer 242 having a Y-shaped channel 246 similar to the Y-shaped channel 228 defined by the shunt retainer 114. In this embodiment, however, the shunt retainer 242 may define a slot 244 as opposed to the opening 150 of the shunt retainer 114. The slot 244 may accommodate different degrees of movement of the shunt retainer 242 about a retractor device 100 as indicated. Another embodiment of a shunt retainer 250, shown in FIG. 19, similarly includes a Y-shaped channel 254, and a rectangular opening 252 which may also accommodate different degrees of movement of the shunt retainer 250.

Figure 20:
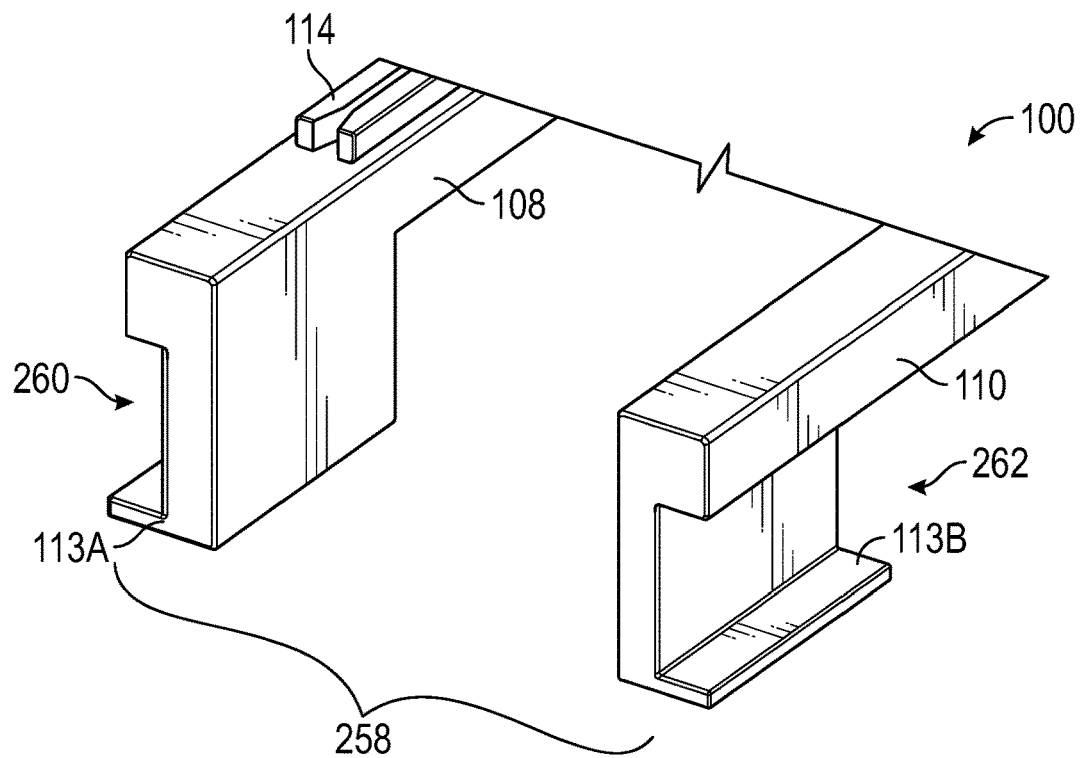
FIG. 20 is a perspective view depicting a first embodiment of a pair of retraction ends for use with the retractor device of FIG. 1, according to aspects of the present disclosure.
Figure 21:
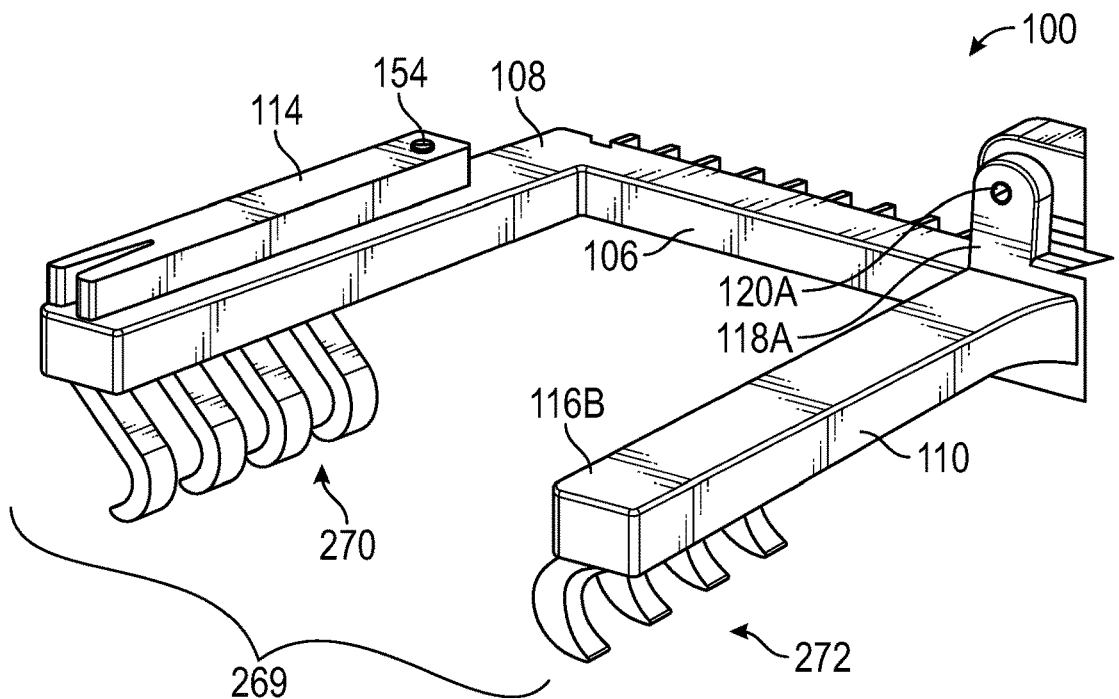
FIG. 21 is a perspective view depicting a second embodiment of a pair of retraction ends for use with the retractor device of FIG. 1, according to aspects of the present disclosure.

Referring to FIG. 20, the combination of the first retracting end 113A and the second retracting end 113B of the retractor device 100 may define a simplified 1×1 retracting teeth array 258 defining a first retraction surface 260 along the first retracting end 113A and a second retraction surface 262 along the second retracting end 113B. Each of the first retracting surface 260 and the second retracting surface 262 may be around or about 1 inch in length by around or about 0.4 inches in depth. The tips of the first retracting surface 260 and the second retracting surface 262 may be rounded at around or about 0.030 inches to allow adequate penetrations of the hypodermis. As show in FIG. 21, in some embodiments, the retractor device 100 may be equipped with a 4×2 retracting teeth array 269 in addition to or in lieu of the first and second retracting surfaces 260 and 262. In this embodiment, the 4×2 retracting teeth array 269 defines a first set of curved teeth 270 along the second segment of the retractor body 104, and a second set of curved teeth 272 along the elongated portion 116B of the arm 110. Other numbers of teeth 272 and configurations or arrangements are also contemplated to meet needs or requirements of the end user.

Returning to FIGS. 1-12, the retractor device 100 of the present disclosure provides several features that are believed to be unique to neurosurgical retractors. The linear retraction provided by the non-metallic components of the ratchet assembly 112, the retractor body 104, and the arm 110 allow a surgeon to retract the retractor device 100 with one hand and guide the first retracting end 113A and the second retracting end 113B along an incision with the other hand. The button 126 locks in place along the rack portion 132 using the tension of the flexible member 138 around the pawl portion 166 of the button 126. The non-metallic retractor device 100 minimizes interference with EM systems unlike conventional metal retractors. The shunt retainer 114 is capable of fully occluding the shunt 240 after placement thus preventing its movement in or out of ventricles.

Testing

Diligent testing of the retractor device 100 was conducted during design-selection of the retractor device 100 and post design-selection which support the novelty of the present concept and highlights the mechanical abilities of the non-metallic retractor device 100. For example, the retractor device 100 was subjected to bending strength checks, screw shear strength checks, user acceptance tests, and shunt retainer strength tests. Chicken and cadaver models were used to gauge and test the retraction of the non-metallic retractor device 100. Chicken models are used to train medical professionals with suturing and other tissue manipulation procedures. This is due to chicken's comparable skin and connective tissue to that of the scalp. Thus, a raw chicken was used to model 1" and 2" scalp incisions. The retractor device 100 was placed in each incision and opened until the resistance of the skin prevented further retraction. These incisions were made at different locations on the chicken to ensure the retractor device 100 was able to function under various skin profiles due to the amount of connective tissue under the skin. These tests indicated the design of the instant retractor device 100 was capable of self-retaining and exhibited comparable performance to the metallic Weitlaner retractor, a conventional retractor.

In conjunction with the chicken model, another concept validation test was performed using human cadavers. The results were consistent with those seen in the chicken test and indicated that the concept would function as intended. A retractor endurance test was further conducted to analyze the ability of the retractor device 100 by wrapping rubber bands around the retractor device 100 in the open configuration 158 to simulate a uniform skin load of 6.2 lbs on the 1×1 retracting teeth array 258. Once loaded with rubber bands, the retractor device 100 was left for four hours and displayed a small degree of elastic bending under load, but retained a constant retraction position for the entire test duration without plastically deforming. In particular, it was revealed that the retracting ends 113A and 113B of the retractor device 100 can withstand approximately 340 lbf of bending load during retraction.

A shunt retainer strength test was further conducted to assess possible scenarios where the shunt retainer 114 extends over a wound and may contact other tools or snag gloves during a procedure. A strength test was performed on the shunt retainer 114 subassembly to determine if and where component failure occurs. A shunt occlusion test was performed on two shunt specimens to account for any variation between tubing. Overall, the aforementioned testing reflected positively upon the system 100 and the retractor device 100 as a non-metallic substitute for a surgical retractor device.

As noted above, the retractor device 100 may define further features and embodiments. For example, in some embodiments, any one of the aforementioned securing members may be sterilized within gamma radiation so that the securing members are suitable for surgical procedures using EM systems.

In some embodiments, the fully assembled retractor device 100 has an overall length of 5.75" and the second segment 108 and the arm 110 may have a substantially fixed length. However, it is contemplated that the second segment 108 and/or the arm 110 may be much longer or shorter than the current figures as depicted to accommodate the patient's anatomy and the operator's preference. Moreover, the second segment 108 and/or the arm 110 may be configured to have an adjustable length. For example, in one non-limiting embodiment, the second segment 108 and/or the arm 110 may include a telescoping system configured for adjusting respective lengths of the second segment 108 and/or the arm 110.

The surfaces of the retractor device 100 and various components are depicted as substantially smooth. However, it is contemplated that the nonmetal retractor device 100 may have surface features such as ridges, bumps, protrusions, channels or any combination of these elements without departing from the scope of the disclosure. These features may be advantageous for interacting with the subject's skin and muscle tissue and substantially increasing gripping capacity. In addition, these features may be dispersed across the device in any known configuration to the preference of the user.

The retractor device 100 may be manufactured using 3D printing methods by printing and connecting various discrete components, injection molding, or by unitary construction or combinations thereof. Indeed, the device's structure suits 3D printing methods because it is relatively inexpensive to print, and retains the structural integrity of non-3D printed devices. It is also contemplated that the nonmetal retractor device 100 may have a mirrored configuration to what is depicted in the figures, which would allow the device to be used from the right or the left side of the incision. Alternatively, the arm 110 and the second segment 108 may extend along different angles, either independently or parallel to each other. In some embodiments, the retractor device 100 may be manufactured such that any interior part of the device is hollow. For example, the retractor body 104 may be constructed hollow so that is a lighter weight and uses less manufacturing material.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A medical device, comprising:
a retractor body defining a proximal portion and a distal portion opposite the proximal portion, the retractor body comprising:
a first segment defined along the proximal portion of the body, and
a second segment defined along the distal portion of the body, the second segment defining a first retracting end;
an arm in sliding engagement with the first segment of the retractor body, the arm defining a second retracting end oriented in parallel relation relative to the first retracting end;
a ratchet assembly, comprising:
a rack portion defined along the first segment of the retractor body, and
a button coupled to a shoulder portion of the arm, the button defining a pawl portion;
a locking mechanism defined along the shoulder portion of the arm for biasing the pawl portion of the button to engage with the rack portion,
wherein the retractor body, the arm, and the ratchet assembly comprise a non-metallic material
a plurality of mounts oriented in parallel relation along the shoulder portion of the arm, the plurality of mounts defining a plurality of respective apertures aligned along a central axis,
a button aperture formed laterally through the button, the button aperture aligned along the central axis between the plurality of respective apertures; and
a securing member passing through the plurality of respective apertures and the button aperture to mount the button in axial rotational engagement with the securing member, wherein the locking mechanism comprises a flexible member stretched around the pawl portion of the button.

2. The medical device of claim 1, wherein the non-metallic material includes a glass fiber material.

3. The medical device of claim 1, further comprising:
a shunt retainer mechanically coupled to the second segment of the retractor body, the shunt retainer configured to move over the second segment of the retractor body.

4. The medical device of claim 3, wherein the second segment includes a slot such that the shunt retainer is slideable over the second segment along the slot.

5. The medical device of claim 3, wherein the shunt retainer comprises:
a base defining a first lateral side and a second lateral side opposite the first lateral side;
a first member extending from the first lateral side of the base; and
a second member extending from the second lateral side of the base, the second member oriented in parallel relation relative to the first member.

6. The medical device of claim 5, further comprising:
a Y-shaped channel defined between the first member and the second member of the shunt retainer, the Y-shaped channel defining a proximal section and a distal section wider than the proximal section; and
wherein the shunt retainer is configured to receive a shunt tubing through the distal section of the Y-shaped channel and occlude the shunt tubing along the proximal section of the Y-shaped channel.

7. The medical device of claim 1, further comprising:
a paddle portion defined along the button;
a tip defined along the pawl portion of the button; and
a plurality of angled slots defined by the rack portion,
wherein the locking mechanism biases the tip of the pawl portion to within an angled slot of the plurality of angled slots of the rack portion, and
wherein actuating the paddle portion of the button temporarily releases the tip of the pawl portion outside of the plurality of angled slots.

8. The medical device of claim 1, wherein the arm is slideable freely over the rack portion of the first segment of the retractor body when the button depressed.

9. The medical device of claim 1, wherein the first retracting end defines a single retraction surface.

10. The medical device of claim 1, wherein the locking mechanism comprises a compression spring, a torsion spring, a die spring, or a deflection-based pawl to forcibly bias a tip of the pawl portion within an angled slot defined along the rack portion.

11. A method, comprising:
forming a retractor body, the retractor body defining a first segment and a second segment in orthogonal relation relative to the first segment;
forming an arm, the arm including a shoulder portion defining a channel;
positioning the first segment of the retractor body through the channel of the arm such that the arm is in movable engagement along the first segment of the retractor body;
forming a ratchet assembly, comprising:
  forming a linear rack portion along the first segment of the body,
  mounting a button to the shoulder portion of the arm such that the button is rotatable axially over the linear racket portion, and
  biasing a pawl portion of the button within the linear rack portion,
wherein the body, the arm, and the ratchet assembly comprise a non-metallic material;
coupling a handle to the retractor body; and
sliding the arm along the first segment of the retractor body using a sole hand of a user by gripping the handle and depressing the button with the sole hand.

12. The method of claim 11, further comprising:
forming the retractor body and the arm entirely from a polymer-based biocompatible material.

13. A method, comprising:
forming a retractor body, the retractor body defining a first segment and a second segment in orthogonal relation relative to the first segment;
forming an arm, the arm including a shoulder portion defining a channel;
positioning the first segment of the retractor body through the channel of the arm such that the arm is in movable engagement along the first segment of the retractor body;
forming a ratchet assembly, comprising:
  forming a linear rack portion along the first segment of the body,
  mounting a button to the shoulder portion of the arm such that the button is rotatable axially over the linear racket portion, and
  biasing a pawl portion of the button within the linear rack portion,
wherein the body, the arm, and the ratchet assembly comprise a non-metallic material;
engaging a shunt retainer along the retractor body;
moving the shunt retainer to a first position relative to the retractor body such that a portion of the shunt retainer extends outside a footprint of the body, the shunt retainer configured to receive a shunt tubing when oriented in the first position; and
moving the shunt retainer to a second position relative to the body such that the shunt retainer is entirely disposed over a footprint of the body to store the shunt retainer.

* * * * *